United States Patent [19]

Hoye et al.

[11] Patent Number: 5,677,467

[45] Date of Patent: Oct. 14, 1997

[54] SYNTHESIS OF ACETOGENINS

[75] Inventors: Thomas R. Hoye, St. Paul; Zhixiong Ye, Minneapolis, both of Minn.

[73] Assignee: Regents of the University of Minnesota, Minneapolis, Minn.

[21] Appl. No.: 724,858

[22] Filed: Oct. 3, 1996

[51] Int. Cl.$^6$ .................... C07D 307/58; C07D 307/12
[52] U.S. Cl. ............................. 549/320; 549/472
[58] Field of Search ........................... 549/320, 472

[56] References Cited

U.S. PATENT DOCUMENTS 5,587,491  12/1996  Hoye et al. ............................. 549/320

OTHER PUBLICATIONS

Hoye and Ye, J. Am. Chem. Soc., 118, pp. 1801-1802 1996.
K. I. Ahammadsahib, et al., "Mode of Action of Bullatacin: A potent antitumor and Pesticidal Annonaceous Acetogenin", Life Sci., 53, 1113-1120, (1993).
Andre Cave, et al., "Recent Advances in the Acetogenins of Annonaceae", Recent Advances in Phytochemistry, vol. 27, Phytochemical Potential of Tropical Plants, Chapter 8, Plenum Press, NY, 167-202, (1993).
Mauro Degli Esposti, et al., "Natural Substances (acetogenins) from the family Annonaceae are Powerful Inhibitors of Mitochondrial NADH dehydrogenase (Complex I)", Biochem. J., 301, 161-167, (1994).
Xin-ping Fang, et al., "Annonaceous Acetogenins: An Updated Review", Phytochemical Analysis, 4, 27-48, (1993).
Xin-ping Fang, et al., "Annonaceous Acetogenins: An Updated Review -Appendices", Phytochemical Analysis, 4, 49-67, (1993).
Xin-Ping Fang, et al., "Gigantetrocin and Gigantriocin: Two Novel Bioactive Annonaceous Acetogenins from Goniothalamus Giganteus", Heterocycles, 32, 11-17, (1991).
Bruno Figadere, et al., "Synthesis of 2,33-Dihydro-4-Oxo-Murisolin: Conjugate Addition of Primary Alkyl Iodides to a,b-Unsaturated Ketones", Tetrahedron Letters, 33, 5189-5192, (1992).
Zhe-Ming Gu, et al., "Annonaceous Acetogenins", Recent Advances in Phytochemistry, vol. 29, Phytochemistry of Medicinal Plants, J.T. Arnason et al., eds. Plenum Press, NY, 249-310, (1995).
Zhe-ming Gu, et al., "Bullacin: A New Cytotoxic Annonaceous Acetogenin from Anona Bullata", Heterocycles, 36, 2221-2228, (1993).
Thomas R. Hoye, et al., "An Efficient and Versatile Synthesis of the Bulenolide Subunit of 4-Hydroxylated Annonaceous Acetogenins", Tetrahedron Letters, 35, 7517-7520, (1994).
Thomas R. Hoye, et al., "On the Stereochemistry of the Bistetrahydrofuranyl Moiety of Uvaricin: Proton Chemical Shifts Can Play a Crucial Role in Complex Structure Determination", J. Am. Chem. Soc., 109, 4402-4403, (1987).
Thomas R. Hoye, et al., "Synthesis of (-) -Bullatacin: The Enantiomer of a Potent, Antitumor, 4-Hydroxylated, Annonaceous Acetogenin", Tetrahedron Letters, 34, 5043-5046, (1993).

Thomas R. Hoye, et al., "Synthesis of (+)-(15,16,19,20,23, 24)-hexepi-Uvaricin: A Bis(tetrahydrofuranyl) Annonaceous Acetogenin Analogue", J. Am. Chem. Soc., 113, 9369-9371, (1991).
Thomas R. Hoye, et al., "Total Synthesis of the Potent Antitumor, bis-Tetrahydrofuranyl Annonaceous Acetogenins (+)-Asimicin and (+)-Bullatacin", Tetrahedron Letters, 36, 1981-1984, (1995).
Y.-H. Hui, et al., "Bullatacin and Bullatacinone: Two Highly Potent Bioactive Acetogenins from Annona Bullata", J. of Nat. Products, 52, 463-477, (1989).
Ulrich Koert, "Total Synthesis of (+)-Rolliniastatin I", Tetrahedron Letters, 35, 2517-2520, (1994).
Mark A. Lewis, et al., "Inhibition of Respiration at Site I by Asimicin, an Insecticidal Acetogenin of the Pawpaw, Asimina Triloba (Annonaceae)", Pesticide Biochemistry and Physiology, 45, 15-23, (1993).
Michael Londershausen, et al., "Molecular Mode of Action of Annonins", Pestic. Sci.33, 427-438, (1991).
Hidefumi Makabe, et al., "Total Synthesis of Solamin and Reticulatacin", J. Chem. Soc. Perkin Transactions 1,, 1975-1981, (1994).
D. James Morre, et al., "Mode of Action of Bullatacin, a Potent Antitumor Acetogenin: Inhibition of NADH Oxidase Activity of Hela and HL-60, but not Liver, Plasma Membranes", Life Sciences, 56, 343-348, (1995).
Hiroyudi Naito, et al., "The First Total Synthesis of (+)-Bullatacin, a Potent Antitumor Annonaceous Acetogenin, and (+)-(15,24)-bisepi-Bullatacin", J. Org. Chem., 60, 4419-4427, (1995).
Sunil Raynayake, et al., "Parvifloracin and Parviflorin: cytotoxic bistetrahydrofuran acetogenins with 35 carbons from Asimina parviflora (Annonacene)", Can. J. Chem., 72, 287-293, (1994).
Matthew J. Rieser, et al., "Determination of Absolute Configuration of Stereogenic Carbinol Centers in Annonaceous Acetogenins by 1H-and 19F-NMR Analysis of Mosher Ester Derivatives", J. Am. Chem. Soc., 114, 10203-10213, (1992).
J. Kent Rupprecht, et al., "Annonaceous Acetogenins: A Review", J. of Natural Products, 53, 237-278, (1990).
Barry M. Trost, et al., "A Concise Convergent Strategy to Acetogenins (+)-Solamin and Analogues", J. Am. Chem. Soc., 116, 7459-7460, (1994).
Zhu-Jun Yao, et al., "Total Synthesis of (10E,15R,16S,19S, 20S,34R)-Corossoline", Tetrahedron Letters, 35, 157-160, (1994).

*Primary Examiner*—Bernard Dentz
*Attorney, Agent, or Firm*—Schwegman, Lundberg, Woessner & Kluth, P.A.

[57] ABSTRACT

A method for the synthesis of bis-tetrahydrofuranyl annonaceous acetogenins, including the natural products and analogs thereof, is provided which proceeds by the Pd-mediated coupling of a bis-tetrahydrofuranyl-subunit comprising a terminal alkyne, with a (C4)-hydroxybutenolide subunit comprising a terminal vinyl iodide, followed by selective reduction of the resulting enyne.

10 Claims, 3 Drawing Sheets

SYNTHESIS OF ACETOGENINS

This invention was made with the support of grants GM-34492 and GM-35962 awarded by the DHHS. The U.S. Government has certain rights in the invention.

BACKGROUND OF THE INVENTION

The annonaceous acetogenins are a rapidly growing class of natural products that have received considerable attention. See, for example, Z. Gu et al., in *Recent Adv. Phytochem.*, J. T. Arnason et al., eds, Plenum Press; N.Y. (1995); Vol. 29, Ch. 11; A. Cave et al., *Recent Phytochem.*, 27, 167 (1993), and J. K. Rupprecht et al., *J. Nat. Prod.*, 53, 237 (1990). Many members possess a variety of biological effects including potent cytotoxic, antitumor, and pesticidal activities. For example, they can interfere with mitochondrial electron transport processes by interaction with complex I, the multi-protein enzyme, NADH-ubiquinone reductase.

(+)-Asimicin (1) and (+)-bullatacin (2)—bis-tetrahydrofuranyl, 4-hydroxylated, annonaceous acetogenins—represent two of the structurally most complex and biologically potent members of this abundant family of antitumor and pesticidal natural products:

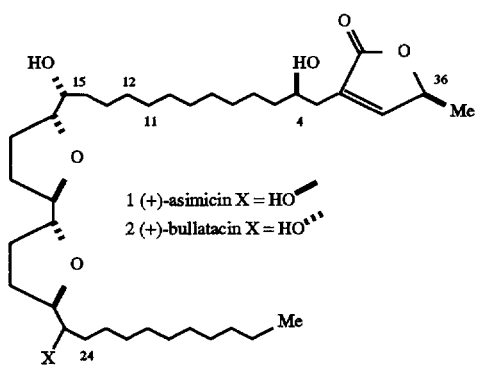

(+)-Bullatacin possesses remarkable levels both of cytotoxicity against many human tumor cell lines, a feature shared by a number of the 4-hydroxylated acetogenins, and in vivo antitumor activity. For example, see J. K. Rupprecht et al., *J. Nat. Prod.*, 53, 237 (1990); X. Fang et al., *Phytoehem. Anal.*, 4, 27 and 49 (1993). Selective inhibition of NADH-oxidase in plasma membrane vesicles isolated from HeLa and HL-60 rumor cells compared to the oxidase from rat liver cells has recently been suggested to contribute to the differential cytotoxicities exhibited by bullatacin. See, D. J. Morré et al., *Life Sci.*, 56, 343 (1995); K. I. Ahammadsahib et al., *Life Sci.*, 53, 1113 (1993); M. Londershausen et al., *Pestic. Sci.*, 33, 427 (1991); and M. A. Lewis et al., *Pestic. Biochem. Physiol.*, 45, 15 (1992).

(+)-Parviflorin (1a), a relatively rare $C_{35}$ adjacent bis-THF acetogenin, was isolated by McLaughlin et al. both from *Asimina parviflora* Duanl. and from *Annona bullata* Rich. See, S. Ratnayake et al., *Can. J. Chem.*, 72, 287 (1994). Parviflorin showed remarkable selectivity in its cytotoxicity against certain human solid minor cell lines. As reported by Z. Gu et al., *Heterocycles*, 16, 2221 (1993), the $ED_{50}$'s for (+)-parviflorin against human A-549 lung carcinoma, MCF-7 breast carcinoma, and HT-29 colon adenocarcinoma are reported to be $1.27\times10^{-15}$, 1.72 and 0.549 µg/mL, respectively.

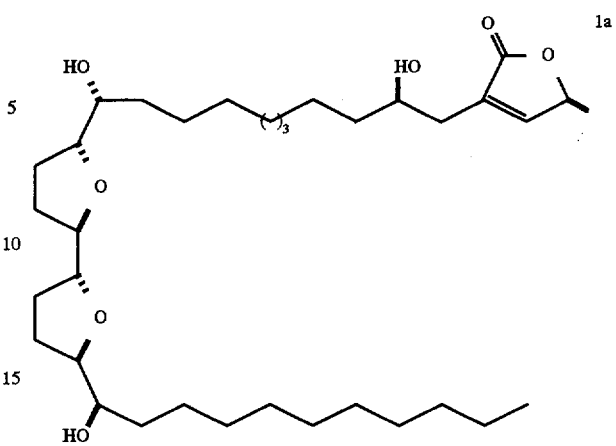

The relative configuration of (+)-parviflorin was elucidated from spectral analysis by Ratnayake et al., cited supra, and the absolute configuration was determined using Mosher methodology by M. J. Rieser et al., *J. Amer. Chem. Soc.*, 114, 10203 (1992). Compound 1a showed very similar spectral data to those of asimicin (1). They share a threo/trans/threo/trans/threo configuration at the THF core and a hydroxyl group at the C(4) position.

At least five syntheses of bis-THF acetogenins or their stereoisomers have recently been reported. For example, see T. R. Hoye et al., *J. Am. Chem. Soc.*, 113, 9369 (1991); T. R. Hoye et al., *Tetrahedron Lett.*, 34, 5043 (1993); U. Koert, *Tetrahedron Lett.*, 35, 2517 (1994); T. R. Hoye, et al., *Tetrahedron Lett.*, 36, 1981 (1995); and H. Naito et al., *J. Org. Chem.*, 60, 4419 (1995).

Other efforts have focused on the simpler mono-THF acetogenin targets. For example, see B. Figadère et al., *Tett. Lett.*, 33, 5189 (1992); Z.-J. Yao et al., *Tett. Lett.*, 35, 157 (1994); H. Makabe et al., *J. Chem. Soc. Perkin Trans I*, 1975 (1994); and B. M. Trost et al., *J. Amer. Chem. Soc.*, 116, 7459 (1994).

However, a continuing need exists for more efficient methods to synthesize the annonaceous acetogenins and their analogs, particularly those which comprise the (C4)-hydroxyl group.

SUMMARY OF THE INVENTION

The present invention provides a method for preparing a bis-tetrahydrofuranyl acetogenin of formula (I):

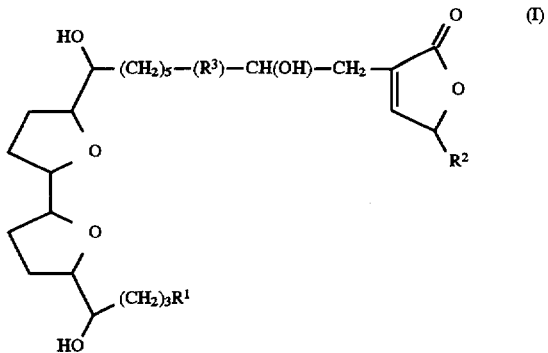

wherein $R^1$, $R^2$ and $R^3$ are alkyl or aryl; comprising:

(a) coupling a vinyl iodide of formula II:

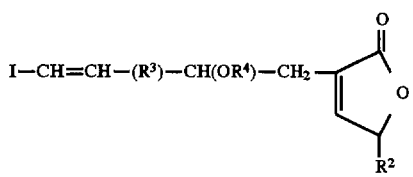

wherein R⁴ is a removable hydroxy protecting group, with a compound of formula (III):

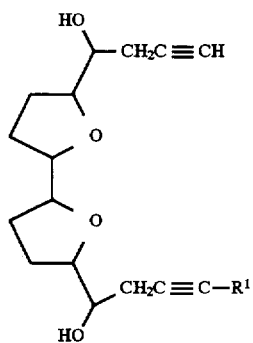

in the presence of an effective amount of palladium catalyst, CuI and a base, in an organic solvent, to yield an enyne of the formula IV:

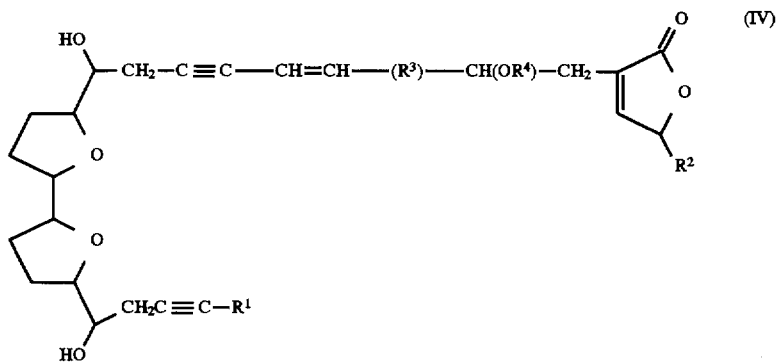

(b) hydrogenating the enyne of formula IV; and (c) and removing the hydroxy protecting group to yield a compound of formula I.

The present invention also provides a method for preparing a bis-tetrahydrofuranyl acetogenin analog of formula (Ia):

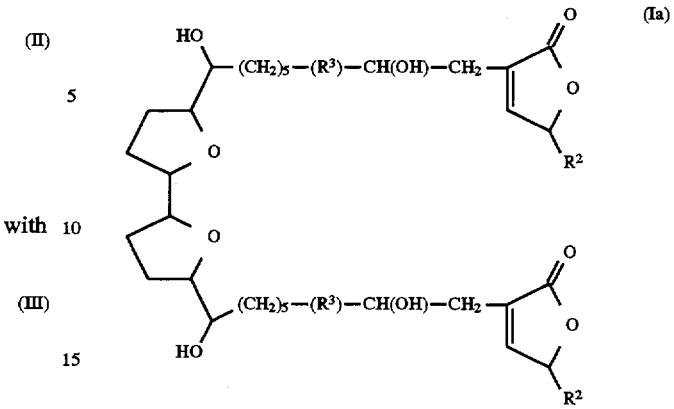

wherein $R^1$, $R^2$ and $R^3$ are alkyl or aryl; comprising:

(a) coupling a vinyl iodide of formula II:

(II)

I—CH=CH—(R³)—CH(OR⁴)—CH₂— wherein R⁴ is a removable hydroxy protecting group, with a compound of formula (IIIa):

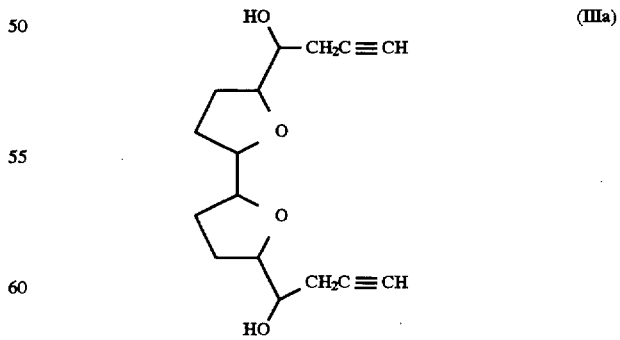

in the presence of an effective amount of palladium catalyst, CuI and a base, in an organic solvent, to yield an enyne of the formula IVa:

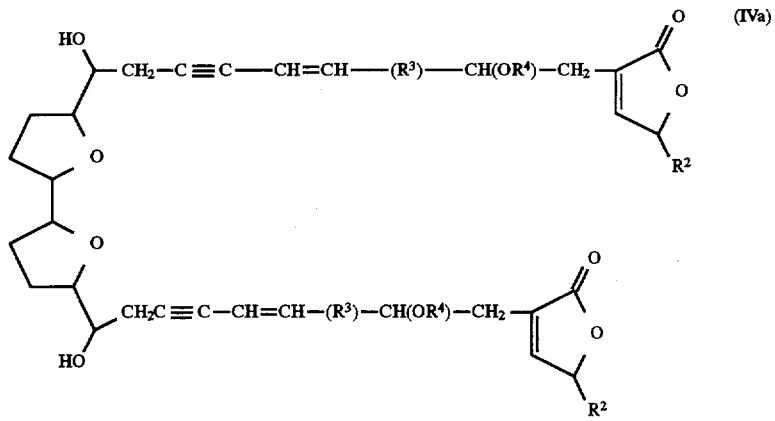

(b) hydrogenating the bis-enyne of formula IVa; and (c) and removing the hydroxy protecting groups to yield a compound of formula Ia.

$R^3$ is preferably a divalent aryl or is alkyl of the formula —$(CH_2)_n$— wherein n is 2–10, preferably 3–7; $R^1$ is preferably ($C_1$–$C_{18}$), most preferably ($C_4$–$C_{10}$)alkyl; and $R^2$ is preferably ($C_1$–$C_4$)alkyl, preferably methyl. Preferably, the tetrahydrofuranyl rings are trans. Thus, the present invention provides an efficient route to the bis-tetrahydrofuranyl annonaceous acetogenins, such as (+)-asimicin, (+)-bullatacin, (+)-parviflorin, their stereoisomers and racemates, and analogs thereof.

The present invention also provides a number of intermediates useful in the synthesis of the compound of formulas (I), (Ia), (II), (III) and (IV), including, but not limited to, compounds of the formula (V):

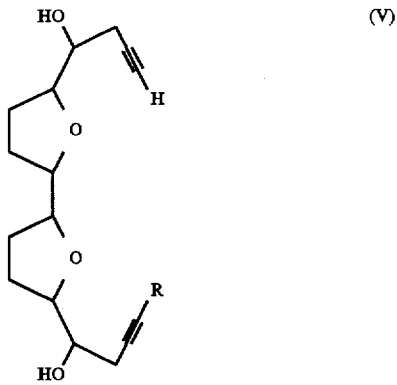

wherein R is H, alkyl or aryl, including compound 3 (FIG. 1) wherein R is $C_7H_{15}$.

The present invention also provides compound of formula VI, preferably those of high optical purity: $R^4$—O—($R^5$)—CH(O$R^7$)—CH$_2$O$R^7$ (VI) wherein $R^5$ is ($C_1$–$C_{22}$)alkyl, preferably —$(CH_2)_n$— wherein n is 1–21 and each $R^4$ or $R_7$ is H or a removable hydroxy protecting group. Such a compound can be prepared by a novel method comprising oxidatively cleaving a compound of the formula (VII): [$R^7$OCH$_2$—CH(O$R^7$)—($R^5$)—O—]$_2$($R^6$), (VII), wherein $R^6$ is a divalent aryl, optionally substituted with ($C_1$–$C_4$) alkyl, such as divalent($C_6$–$C_{14}$)aryl. Preferably $R^6$ is divalent phenyl, such as the 1,4-phenylene group shown in compound 11.

The present invention also provides a compound of formula VIII:

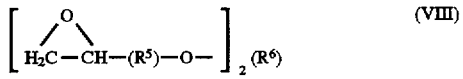

wherein $R^5$ and $R^6$ are as defined for compound VII. A representative compound of this formula is compound 12, wherein ($R^5$) is —$(CH_2)_n$—, n=4 and $R^6$ is 1,4-phenylene.

A novel method to prepare compounds of formula (II), as exemplified in FIG. 2, is also within the scope of the invention.

BRIEF DESCRIPTION OF THE FIGURES

FIG. 3 is a schematic depiction of the synthesis of 1a.

DETAILED DESCRIPTION OF THE INVENTION

The compounds of formulas I–VIII are depicted in accord with standard organic structural formulas, e.g., positions shown as unoccupied are occupied by H. The stereochemistry at the asymmetric carbon atoms is not designated, but may be R or S. Thus, the individual dl-and resolved enantiomers are within the scope of the invention, and may be prepared as described in detail hereinbelow, or in the publications incorporated by reference herein. For example, the two linked tetrahydrofuranyl rings can be (i) both of the trans configuration, as shown in structure 1a or as in (–)-bullatacin, (ii) both of the cis-configuration, or (iii) one of cis and one of trans configuration, for any of the compounds shown above.

The term "alkyl" as used herein encompasses branched- and straight-chain alkyl, i.e., ($C_1$–$C_{22}$)alkyl, as well as cycloalkyl, (cycloalkyl)alkyl and alkyl(cycloalkyl)alkyl of about 4–25 carbon atoms. The term "aryl" as used herein encompasses ($C_6$–$C_{20}$)aryl, including alkaryl, aralkyl or alkarylakyl.

Preferably, $R^2$ is ($C_1$–$C_4$)alkyl, e.g., $CH_3$ or $CH_2CH_3$; $R^3$ is $(CH_2)_n$, wherein n is 2–10; preferably 3–7; e.g., —($C_2$) $_5$—; and $R^1$ is 1–18 , preferably 3–13, i.e., n-decyl.

Removable hydroxy protecting groups are selected from the wide variety of such groups known to the art that are stable (or labile) to the subsequent reaction conditions, as desired. Such groups include tetrahydropyran-2-yl, 2-methoxyethoxy, acetyl, benzyl, substituted benzyl, such as 4-methoxybenzyl; and $Si(R^{10})_3$ wherein each $R^{10}$ is individually $(C_1-C_4)$alkyl or phenyl. For a further discussion of labile hydroxy and carbonyl protecting groups, see U.S. Pat. No. 4,816,586, at Cols. 4–5.

Useful organic solvents are those that are stable to the reagents employed in the present methods, and include tetrahydrofuran, methylene chloride, $CHCl_3$, DMF, DMA, ethers, benzene, toluene, hydrocarbon solvents and, in some cases, alkanols or alkanol/water mixtures.

Bases can be selected from inorganic bases such as carbonates, bicarbonates, borates and hydroxides, or organic bases such as amines, acetates, morpholine, pyridines, tartarates, citrates and the like. Acids include inorganic or organic acids such as $H_2SO_4$, HCl or $BF_3$.etherate, citric acid, acetic acid and the like.

Reductions of carbonyls can be carried out with metal hydride reducing agents and reductions of olefins and acetylenes can be carried out by hydrogenation.

Figure 1:
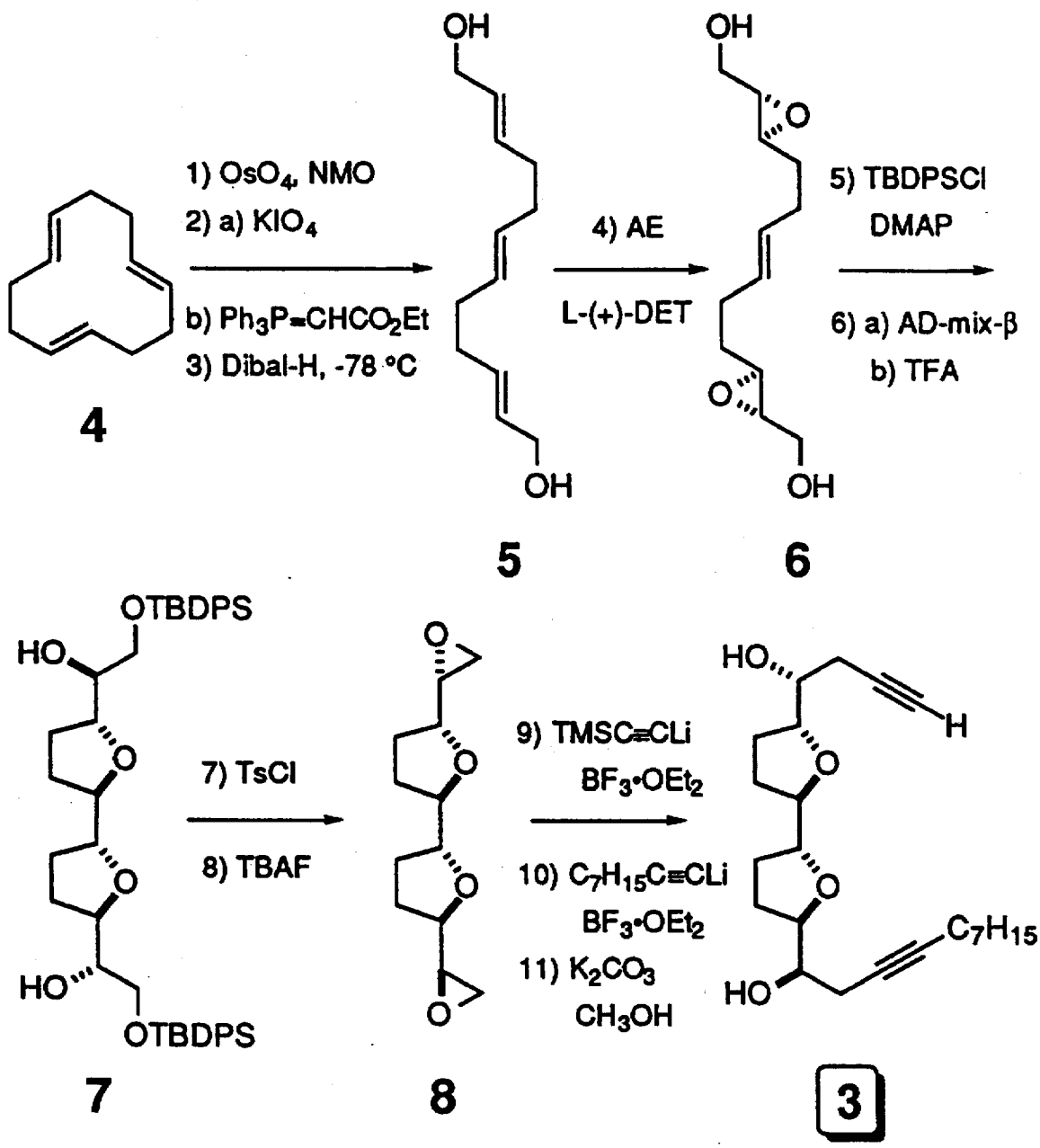
FIG. 1 is a schematic depiction of the synthesis of compound 3.

A wide variety of reagents of the general formula $R^1C \equiv CLi$ can be used in place of the reagent $C_7H_{15}C \equiv CLi$ shown in FIG. 1.

One synthesis of compounds of formula (II) is described in commonly assigned U.S. patent application Ser. No. 08/405,131, filed Mar. 15, 1995.

Conditions for palladium catalyzed addition/elimination reactions are well-known to the art, and can be carried out with Pd(0) catalysts, or with palladium catalysts that are reduced thereto under the conditions of the reactions, such as $Pd(OAc)_2$, $PdCl_2$, and the like. Copper halide salts can promote the coupling of terminal acetylenes with olefinic iodides. Additional Pd catalysts useful in these reactions are disclosed in U.S. Pat. No. 5,233,059.

Taking advantage of the C2-symmetry within the bis-THF subunit, a bidirectional chain synthesis strategy was employed for the construction of compound 3(FIG. 1). Thus, two of the three double bonds in trans,trans,trans-1,5,9-cyclododecatriene (4) were selectively oxidized with N-methyl morpholine-N-oxide (NMO) in the presence of a catalytic amount of osmium tetroxide. Other bulk oxidants such as potassium ferricyanide, iodine and the like, can also be used. Oxidative cleavage of the tetrol with potassium periodate and Wittig extension of the resultant dialdehyde with $Ph_3P=CH-CO_2Et$ gave a bis-enoate. This was reduced with diisobutylaluminum hydride (DIBAL—H) to provide bis-allylic alcohol 5, in 51% overall yield from 4.

The stereogenic centers in the bis-THF backbone were installed by sequential double Sharpless asymmetric epoxidation/Sharpless asymmetric dihydroxylation, a strategy used by D. F. Taber et al., *J. Org. Chem.*, 59, 3442 (1994), in the synthesis of (+)-tuberine. Thus, epoxidation of 5 with L-(+)diethyl tartrate by the procedure of R. M. Hanson et al., *J. Org. Chem.*, 51, 1922 (1986), gave the diepoxide 6 [~97% ee after chromatography; >99% ee (Mosher ester analysis) and 87% yield after recrystallization]. The primary alcohols were silylated with (t-butyl)(diphenyl)silyl chloride (TBDPSCl). Asymmetric dihydroxylation by the procedure of W. Anberg et al., *J. Org. Chem.*, 57, 2768 (1992) then afforded an intermediate diol, which was immediately treated with trifluoroacetic acid to effect an "inside-out" epoxide cascade reaction producing the bis-THF, 7 (85% from 6). Both carbinol centers in 7 were inverted by sequential treatment with TsCl and excess tetrabutylammonium fluoride (TBAF) to produce the threo/trans/threo/trans/threo diepoxide 8 (87% from 7).

Selective opening of the diepoxide 8 with lithium trimethylsilylacetylide (0.5 molar equivalents) in the presence of boron trifluoride etherate by the procedure of M. Yamaguchi et al., *Tett. Lett.*, 27, 803 (1986) and P. Mohr et al., *Tett. Lett.*, 28, 391 (1987) provided a mixture of two useful products incorporating one and two trimethylsilylacetylene units (61% and 14% respectively, based upon recovered starting material). The latter can be used for preparation of $C_2$-symmetric acetogenin analogs. The former, a desymmetrized bis-THF mono-epoxide, was opened with excess 1-lithio-1-nonyne (89%) followed by desilylation to give the terminal alkyne 3 (99%).

Figure 2:
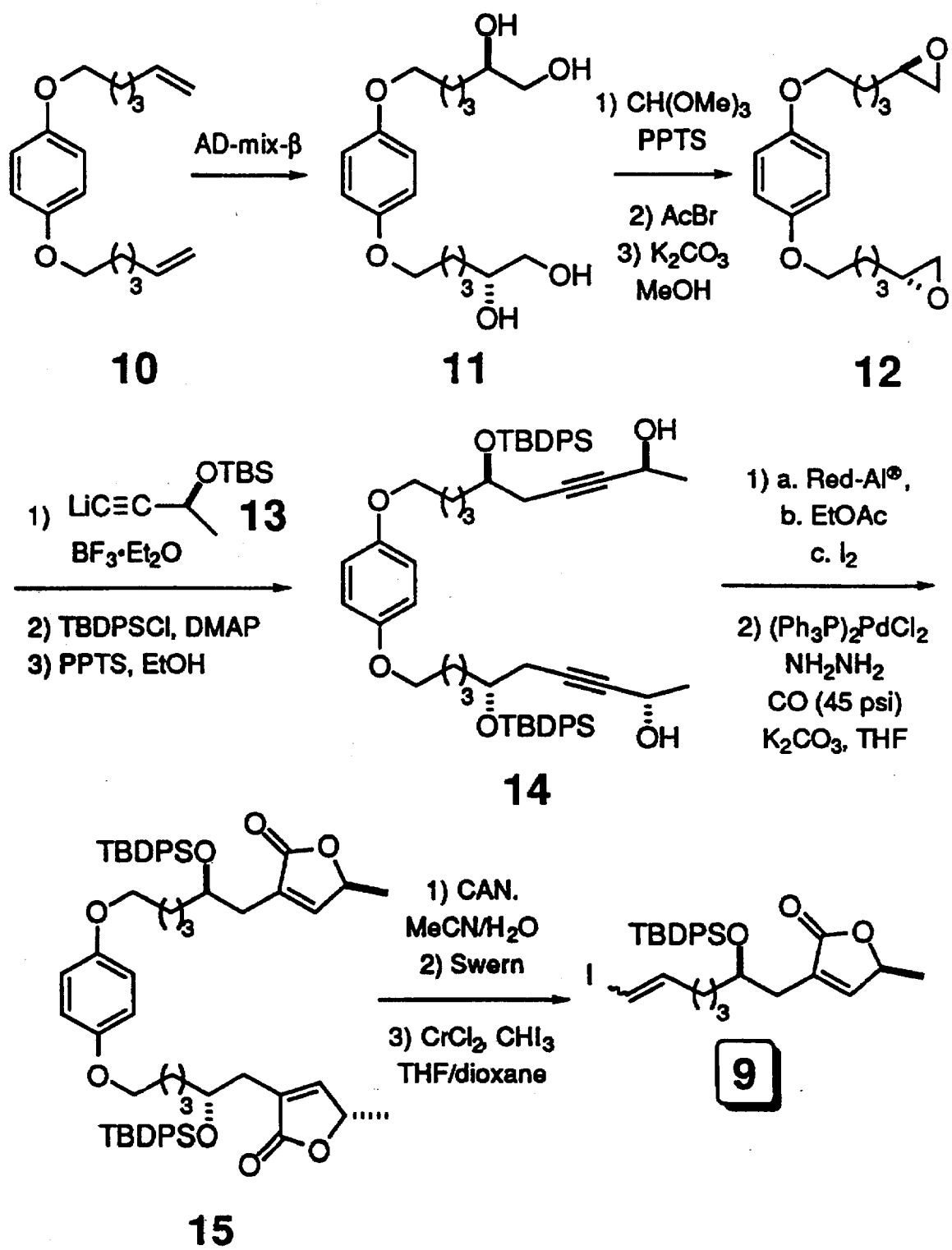
FIG. 2 is a schematic depiction of the synthesis of compound 9.

Vinyl iodide 9 (FIG. 2) was required for coupling with the terminal alkyne 3. The synthesis of 2-(β-hydroxyalkyl)-4-methylbutenolides can be generally accomplished as disclosed by T. R. Hoye et al., *Tett. Lett.*, 35, 7512 (1994). However, the scheme shown in FIG. 2 represents an improved method to prepare enantiomerically pure 1,2-epoxy alkanes that also bear a functional group at their remote terminus. Thus, as shown in FIG. 2, 1,4-bis-alkenyloxybenzene 10 (prepared from bis-alkylation of hydroquinone with 6-iodo-1-hexene in 72% yield) was converted to the corresponding tetrol 11 by double asymmetric dihydroxylation with about 80% ee using AD-mix-β. Tetrol 11, which has two ω-functional-1,2-diol units tethered through the hydroquinone linker, was highly crystalline. Recrystallization from ethyl acetate efficiently returned material of very high optical purity [>99% ee (Mosher analysis), 62% yield]. Tetraol 11 (or a protected version thereof) can also be oxidatively cleaved with CAN, DDQ and the like, to useful compounds of formula VII.

In the efficient procedure of H. Kolb et al., *Tetrahedron*, 43, 10515 (1992), the tetrol 11 was converted into the optically pure bis-epoxide 12 (92%). Opening of 12 with the lithiated optically pure 3-butyn-2-ol derivative 13, silylation (TBDPSCl) of the eventual C(4) hydroxyl group, and selective removal of the t-butyldimethylsilyl (TBS) ether produced the propargylic alcohol 14 (68% from 12). The butenolide 15 was obtained by Red-Al® reduction, iodine treatment, and carbonylation under Stille conditions (81% from 14). T. R. Hoye et al., *Tetrahedron Lett.*, 35, 7517 (1994), J. K. Stille et al., *J. Am. Chem. Soc.*, 102, 4193 (1980). Oxidative release with CAN or other oxidizing agents such as DDQ, then afforded a primary alcohol. Swern oxidation to the corresponding aldehyde and reaction with chromium(II) chloride and iodoform provided the terminal vinyl iodide 9 (68% from 15, 5:1 mixture of E/Z isomers). K. Takai et al, *J. Amer. Chem. Soc.*, 108, 7408 (1986); D. A. Evans et al., *J. Am. Chem. Soc.*, 115, 11446 (1993).

Figure 3:
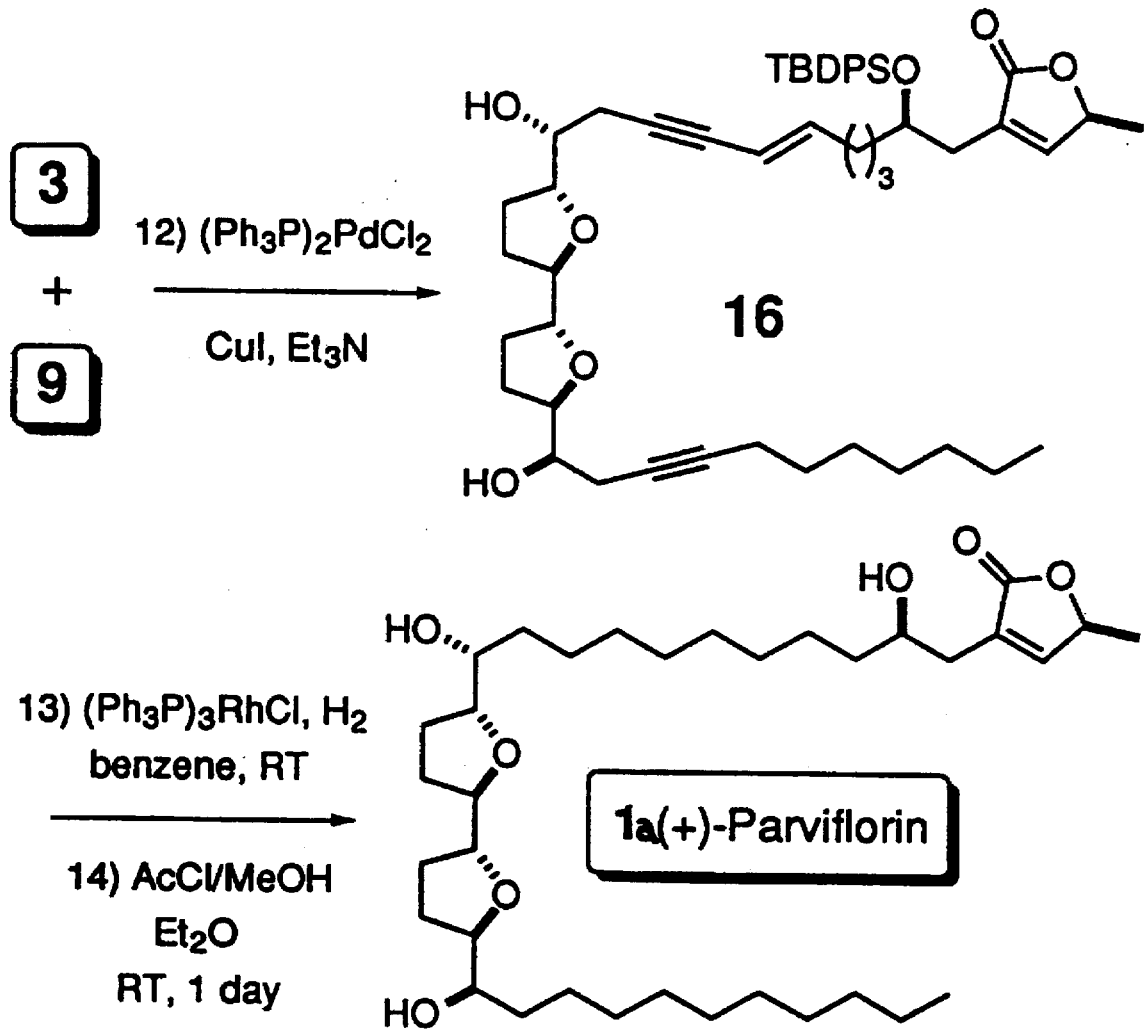

The final Pd(0)-catalyzed coupling of alkyne 3 with vinyl iodide 9 gave the endiyne 16 in 82% yield (FIG. 3). Selective hydrogenation with Wilkinson's catalyst (71%) left the butenolide intact. Desilylation gave (+)-parviflorin (1a, 82%).

Other compounds within the scope of formula I can be readily prepared by modifications of these procedures, and employed as cytotoxic, antitumor and pesticidal agents in vitro and in vivo as disclosed by the Morré et al., Ahammadsahib et al., Londershausen et al. and Lewis et al., cited hereinabove.

The invention will be further described by reference to the following detailed examples.

EXAMPLE 1

Preparation of (E)-9-cyclododecen-1,2,5,6-tetrols (4a)

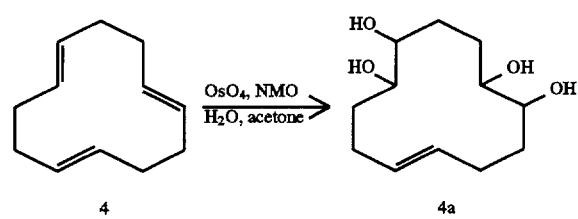

To a mixture of trans,trans,trans-1,5,9-cyclododecatriene 4 (2.05 g, 12.6 mmol), osmium tetroxide (0.2 mL, 2.5% in 2-methyl-2-propanol, 0.02 mmol), acetone (125 mL) and water (25 mL) was added solid N-methylmorpholine-N-oxide (3.70 g, 31.6 mmol) portionwise during a period of a day at room temperature. The reaction was monitored carefully by TLC. Reaction was stopped by the addition of silica gel (5.0 g), and the volatiles were removed under reduced pressure. The residue was eluted through a pad of silica gel with 4:1 ethyl acetate:ethanol to give the alcohol 4a (1.78 g, 61%) as a white solid (mp=180.0°–181.0° C.).

EXAMPLE 2

Preparation of (E)-4-octendial (4b)

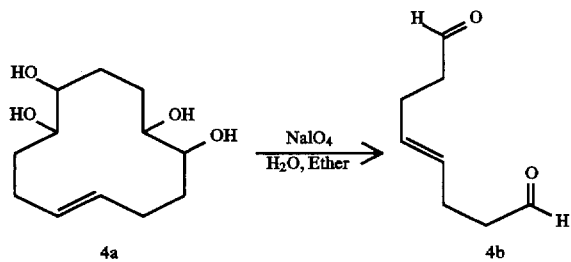

To a mixture of the alcohol 4a (4.54 g, 1.97 mmol), water (9.0 mL), and ether (300 mL) was added sodium metaperiodate (16.2 g, 75.7 mmol) with vigorous stirring at room temperature for 1.5 h. The ether layer was decanted and the solid was dissolved in a minimum amount of water and extracted with methylene chloride (2×50 mL). The combined organic layers were washed with a saturated aqueous sodium chloride solution, dried over anhydrous magnesium sulfate, filtered, and concentrated. The crude product was purified by MPLC (2.3:1 hexane:ethyl acetate) to gave the aldehyde 4b (2.59 g, 94%) as a colorless liquid.

$^1$H NMR (500 MHz, CDCl$_3$): δ9.72 (t, 2H, J=1.3 Hz, CH$_2$C$\underline{H}$O), 5.44 (t, 2H, J=3.4 Hz, C$\underline{H}$=C$\underline{H}$CH$_2$), 2.47 (br t, 4H, J=7.0 Hz, CH$_2$C$\underline{H}_2$CHO), and 2.29 (m, 4H, C$\underline{H}_2$CH=CH).

$^{13}$C NMR (125 MHz, CDCl$_3$): δ202.0, 129.4, 43.3, and 25.0.

EXAMPLE 3

Preparation of diethyl (E,E,E)-dodeca-2,6,10-trienedioate (4c)

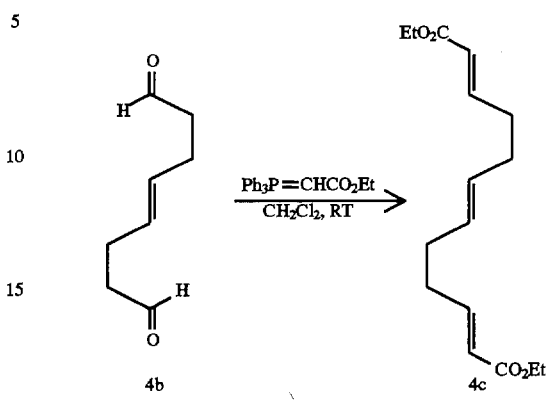

To a solution of the aldehyde 4b (2.49 g, 17.8 mmol) in methylene chloride (100 mL) was added a solution of ethyl (triphenylphosphoranylidene)acetate (17.5 g, 50.2 mmol) in methylene chloride (20 mL) slowly at room temperature. The reaction mixture was kept at room temperature overnight, and the solvent was removed in vacuo. The residue was washed with hexane (3×20 mL). The combined organic solutions were concentrated, and the crude product purified by MPLC (9:1 hexane:ethyl acetate) to give the ester 4c (4.59 g, 91%) as a colorless liquid. Alternatively 4c was made by stirring the mixture of the alcohol 4a and sodium metaperiodate in water/ether at room temperature for 2 h. The volatiles were evaporated and ethyl (triphenylphosphoranylidene)acetate was added. The mixture was stirred at room temperature overnight and worked up in the same fashion (79%).

EXAMPLE 4

Preparation of (E,E,E)-dodeca-2,6,10-triene-1,12-diol (5)

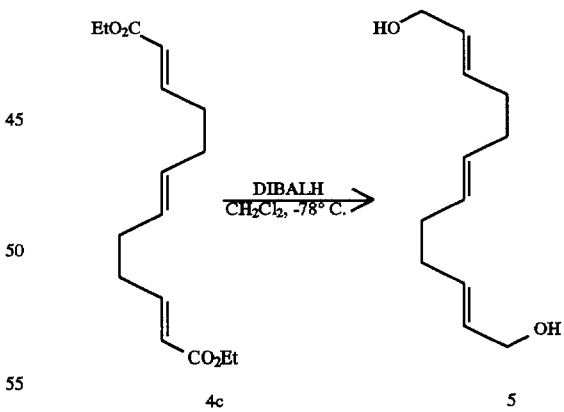

The solution of the ester 4c (4.01 g, 14.3 mmol) in methylene chloride (100 mL) was cooled to −78° C. and diisobutylaluminium hydride (16.0 g, 11.2 mmol) was added dropwise to the solution. The reaction mixture was stirred at −78° C. for 1.5 h and it was quenched with methanol (30 mL) followed by addition of saturated aqueous ammonium chloride solution (50 mL). The mixture was then warmed slowly to room temperature. The solid was filtered and washed with methylene chloride (3×50 mL). The combined organic layers were dried over anhydrous magnesium sulfate, filtered, and concentrated. The residue was purified by MPLC to give the alcohol 5 (2.71 g, 97%) as a white solid (mp=37.0°–38.0° C.).

EXAMPLE 5

Preparation of (−)-{2S-[2α,3β[3E,6(1R*,2R*)]]}-3-{6-[2-(hydroxymethyl)oxiranyl]-3-hexenyl}oxiranemethanol (6)

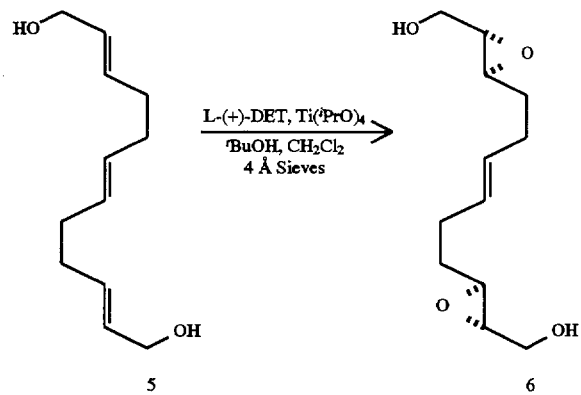

An oven-dried 15 mL three-necked round-bottomed flask equipped with a magnetic stirbar and thermometer was charged with 4 Å powered, activated molecular sieves (500 mg) and methylene chloride (150 mL, dried over $CaH_2$). The flask was cooled to −20° C., L-(+)-diethyl tartrate (2.65 g, 12.8 mmol) and Ti($^i$PrO)$_4$ (2.10 g, 7.39 mmol) were added sequentially via syringe under dry Ar. The reaction mixture was stirred at −20° C. and tert-butylhydroperoxide (11.0 mL, 5.17M in isooctane, 56.9 mmol) was added through a syringe at a moderate rate. The solution was stirred at −20° C. for 30 min, and the alcohol 5 (1.52 g, 7.72 mmol) in methylene chloride (30 mL) was added dropwise over a period of 30 min being careful to maintain the reaction temperature between −20° to −15° C. The mixture was stirred for an additional 2 h at −20° to −15° C. A sodium hydroxide solution (10 mL, aq 10% w/v) was added to the reaction mixture. The mixture was allowed to warm to room temperature, stirred for 1 h, and filtered through Celite®. The solid was washed with ethyl acetate (3×50 mL). The combined organic solutions were dried over anhydrous magnesium sulfate, filtered, and concentrated to yield a yellowish solid. The crude product was purified by flash chromatography and recrystallized from ethyl acetate to give the alcohol 6 (1.52 g, 87%) as a white solid (mp =119.5°–120.0° C.).

EXAMPLE 6

Preparation of (−)-{2S-[2α,3β[3E,6(1R*,2R*)]]}-3-{6-[2-[[(1,1-dimethylethyl)diphenylsilyl]oxy]methyl]oxiranyl]-3-hexenyl}oxiranemethanol-α-{[(1,1-dimethylethyl)diphenyl]silylether} (6a)

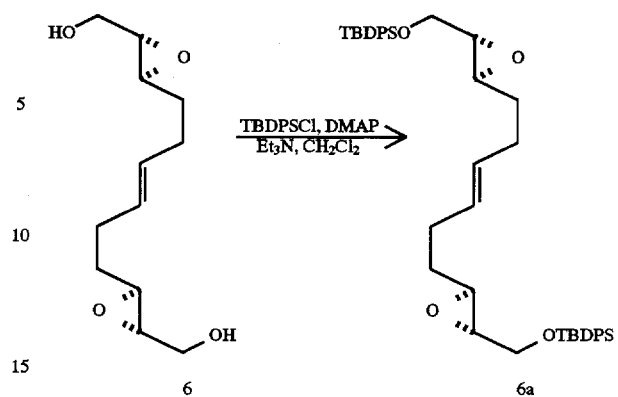

To a stirred solution of the alcohol 6 (42.2 mg, 0.185 mmol) in methylene chloride (4.0 mL) was sequentially added triethylamine (163 mg, 1.61 mmol), 4-(N,N-dimethylamino)pyridine (16.0 mg, 0.131 mmol) and tert-butyldiphenylsilylchloride (123 mg, 0.446 mmol). After being stirred at room temperature overnight, the reaction mixture was quenched with brine. The organic layer was separated and the aqueous layer was extracted with chloroform (3×10 mL). The combined organic layers were dried over anhydrous magnesium sulfate, filtered, and concentrated. The residue was purified by flash chromatography (9:1 hexane:ethyl acetate) to give the olefin 6a (125 mg, 96%) as a colorless oil; tlc: $R_f$=0.32 in 9:1 hexane:ethyl acetate; $[α]_D^{RT}$=−19.4°, c=5.61 in ethyl acetate.

EXAMPLE 7

Preparation of (−)-{2S-[2α,3β[3S*, 4S*,6(1R*,2R*)]]}-3-{6-[2-[[[(1,1-dimethylethyl)diphenylsilyl]oxy]methyl]oxiranyl]-3,4-dihydroxyhexanyl}oxiranemethanol-α-{[(1,1-dimethylethyl)diphenyl]silylether} (6b)

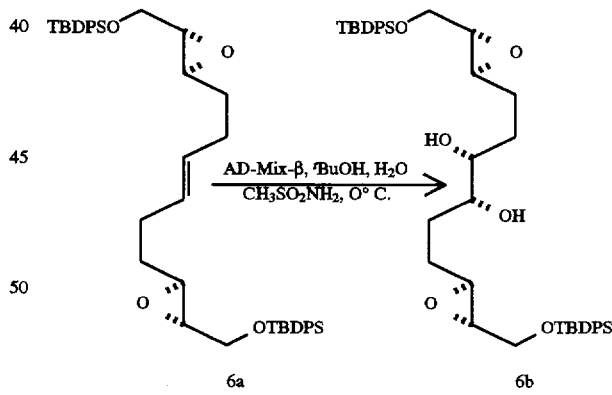

A 5 mL round-bottom flask was charged with tert-butyl alcohol (1 mL), water (1 mL), and AD mix-β (0.34 g). The reaction mixture was stirred at room temperature and produced two clear phases. Methanesulfonamide (24.8 mg) was then added. The mixture was cooled to 0° C., the olefin 6a (104 mg, 0.148 mmol) was added, and the heterogeneous slurry was stirred vigorously at 0° C. for 5 h (progress was monitored by TLC). While the mixture was stirred at 0° C., solid sodium sulfite (0.5 g) was added. The mixture was allowed to warm to room temperature and stirred for an additional 30 min. Ethyl acetate (5 mL) was added to the reaction mixture. After separation of the layers, the aqueous phase was further extracted with ethyl acetate (3×5 mL). The combined organic layers were washed with a 2N NaOH solution, dried over anhydrous magnesium sulfate, filtered, and concentrated. The crude product was purified by MPLC (1.5:1 hexane:ethyl acetate) to give the alcohol 6b (99.5 mg, 91%) as a colorless oil; tlc: $R_f$=0.39 in 1:1 hexane:ethyl acetate; $[\alpha]_D^{RT}$=−6.5°, c=5.44 in ethyl acetate.

EXAMPLE 8

Preparation of (+)-{2R-[2α[2'R*,5'R*(S*)],5β(S*)]}-α,α'-di{[[(1',1'-dimetylethyl)diphenylsilyl]oxy]methyl}octahydro[2,2'-bifuran]-5,5'-dimethanol (7)

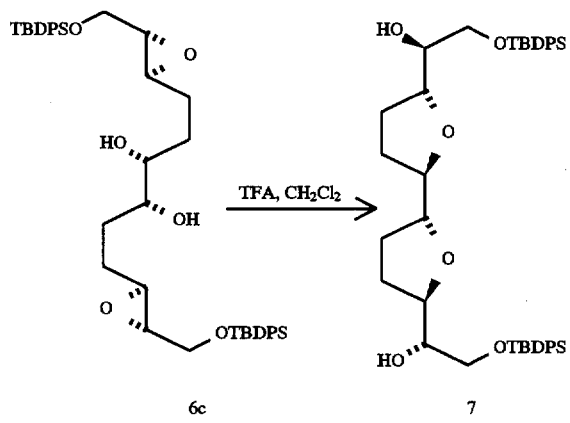

To a solution of the alcohol 6c (751 mg, 1.02 mmol) in methylene chloride (5.0 mL) was added trifluoroacetic acid (0.2 mL) dropwise at room temperature. The reaction mixture was stirred for one hour at room temperature, quenched with a saturated aqueous sodium bicarbonate solution, and extracted with methylene chloride (3×10 mL). The combined organic extracts were washed with brine, dried over anhydrous magnesium sulfate, filtered, and concentrated. The crude product was purified by MPLC (2.3:1 hexane:ethyl acetate) to give the alcohol 7 (726 mg, 97%) as a colorless oil. Compound 7 was also synthesized by following the procedure of asymmetric dihydroxylation. Sodium sulfite was added at 0° C. and the mixture was warm to room temperature. TFA was added and stirred for 6 h (81%) or stirred at room temperature for 24 h (73%) without TFA. The mixture was work up by standard procedure; tlc: $R_f$=0.61 in 1:1 hexane:ethyl acetate; $[\alpha]_D^{RT}$=+5.6°, c=9.10 in ethyl acetate.

EXAMPLE 9

Preparation of (−)-{2R-[2α[2'R*,5'R*(S*)],5β(S*)]}-α,α'-di{[[(1',1'-dimethylethyl)diphenylsilyl]oxy]methyl}octahydro-[2,2'-bifuran]-5,5'-dimethanol, bis(4-methylbenzenesulfonate) (7a)

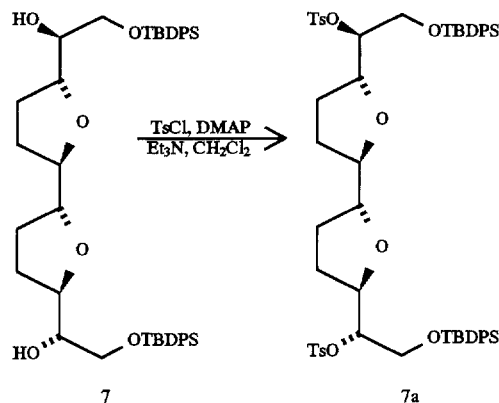

To a stirred solution of the alcohol 7 (651 mg, 0.881 mmol) in methylene chloride (5.0 mL) was sequentially added triethylamine (1.2 mL), 4-(N,N-dimethylamino)pyridine (63 mg, 0.52 mmol), and p-toluenesulfonyl chloride (753 mg, 3.95 mmol). The reaction mixture was stirred at 55° C. for 24 h, and quenched with brine. The organic layer was separated, and the aqueous layer was extracted with ethyl acetate (3×10 mL). The organic layers were combined, dried over anhydrous magnesium sulfate, filtered, and concentrated. The crude product was purified by MPLC (3:1 hexane:ethyl acetate) to give the toluenesulfonate 7a (866 mg, 94%) as a colorless oil; IR (neat, thin layer): 3068, 3048, 2963, 2933, 2863, 1965, 1907, 1825, 1737, 1595, 1464, 1432, 1360, and 1301 cm$^{-1}$; Anal. Calcd for $C_{44}H_{58}O_6Si$: C, 66.51%; H, 6.74%. Found: C, 66.38%; H, 6.83%; tlc: $R_f$=0.41 in 2:1 hexane:ethyl acetate; $[\alpha]_D^{RT}$=−21.8°, c=5.28 in ethyl acetate.

EXAMPLE 10

Preparation of (−)-{2R-[2α[2'R*,5'R*(R*)],5β(R*)]}-5,5'-dioxiranyloctahydro-2,2'-bifuran (8)

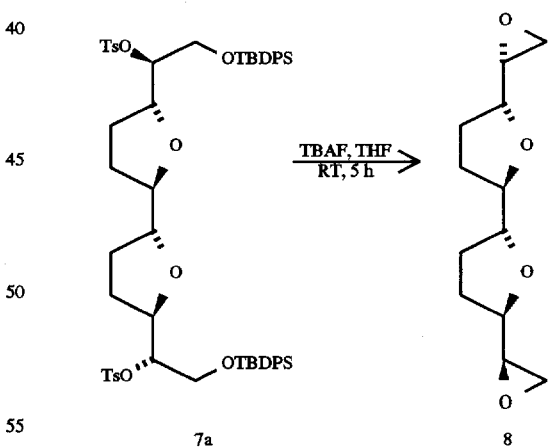

To a solution of the toluenesulfonate 7a (275 mg, 262 μmol) in tetrahydrofuran (5.0 mL) was added a tetrabutylammonium fluoride solution (1.0 mL, 1.0M in tetrahydrofuran, 1.0 mmol). The reaction mixture was stirred at room temperature for 2 h, and concentrated to leave a crude oil. The crude product was purified by flash chromatography (1:2 hexane:ethyl acetate) to give the epoxide 8 (65.1 mg, 93%) as a colorless oil.

$^1$H NMR (500 MHz, CDCl$_3$): δ3.76 (dd, 2H, J=10.7 and 4.6 Hz, CHO), 3.72 (ddd, 2H, J=7.0, 7.0, and 4.9 Hz, C HOCHOCH$_a$H$_b$), 2.79 (ddd, 2H, J=4.6, 4.6, and 2.7 Hz, C HOCH$_a$H$_b$), 2.56 (dd, 2H, J=6.2 and 5.3 Hz, CHOC H$_a$H$_b$), 2.51 (dd, 2H, J=5.5 and 2.8 Hz, CHOCH$_a$H$_b$), 1.91–1.97 (m, 2H, from among CH$_2$CH$_2$), 1.80–1.85 (m, 2H, from among CH$_2$CH$_2$), and 1.56–1.70 (m, 4H, from among CH$_2$CH$_2$).

$^{13}$C NMR (125 MHz, CDCl$_3$): δ82.0, 78.8, 54.0, 43.9, 28.7, and 28.1.

IR (neat, thin layer): 3055, 2977, 2877, 1464, 1359, 1301, 1256, 1103, 1060, 1029, 940, and 886 cm$^{-1}$.

Anal. Calcd for C$_{12}$H$_{18}$O$_4$: C, 63.70%; H, 8.02%. Found: C, 63.58%; H, 7.98%.

cap gc: t$_R$=8.85 min; column: 25 m×0.25 mm, OV–101; temp prog: 50° C./4 min/20° C. min$^{-1}$/250° C./0 min. tlc: R$_f$=0.27 in 1:3 haxane:ethyl acetate.

[α]$_D^{RT}$=−15.5°, c=5.24 in ethyl acetate.

EXAMPLE 11

Preparation of (−)-{2R-[2α[2'R*,5'R*(R*)],5β(R*)}-α-[3-(trimethylsilyl)-2-propynyl]octahydro-α'-oxiranyl-[2,2'-bifuran]-5-methanol (8a) and (−)-{2R-[2α[2'R*,5'R*(R*)], 5β(R*)}-α,α'-di[3-(trimethylsilyl)-2-propynyl]octahydro[2, 2'-bifuran]-5,5'-dimethanol (8a')

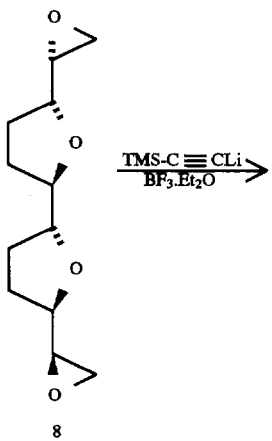

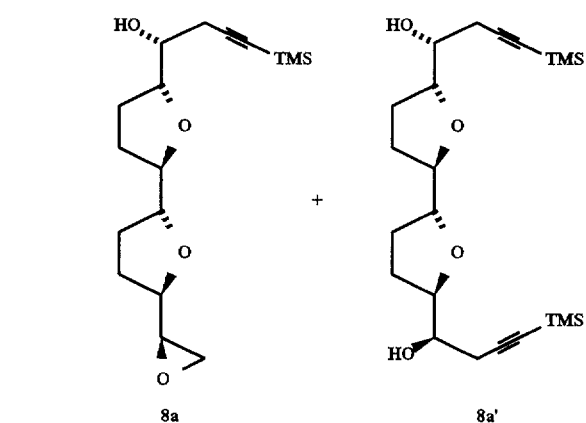

To a solution of trimethylsilylacetylene (113 mg, 1.15 mmol) in dry tetrahydrofuran (2.0 mL) was added n-butyl lithium (450 μL, 2.5M in hexane, 1.13 mmol) at −78° C. The reaction mixture was stirred at −78° C. for 30 min. Boron trifluoride etherate (162 mg, 1.14 mmol) was added slowly. After the reaction mixture was stirred at −78° C. for 15 min, the solution was cannulated into a flask containing a solution of the epoxide 8 (512 mg, 2.26 mmol) in dry tetrahydrofuran (5.0 mL) slowly at −78° C. After 10 min at −78° C., the reaction mixture was poured into a mixture of diethyl ether (10 mL) and saturated aqueous ammonium chloride (10 mL). The layers were separated, and the aqueous layer was extracted with diethyl ether (3×10 mL). The combined organic extracts were washed with brine, dried over anhydrous magnesium sulfate, filtered, and concentrated. The crude products were separated by MPLC (1:1 hexane:ethyl acetate with 3% isopropyl alcohol) to give the alcohol 8a and the diol 8a' as colorless oils [210 mg (61%) and 62.5 mg (14%) respectively, yield is based on the recovered starting material (272 mg, 53%)].

8a:

$^1$H NMR (500 MHz, CDCl$_3$): δ3.97 (ddd, 1H, J=6.1, 6.1, and 1.5 Hz, CH$_2$CHOCHOH), 3.91 (m, 2H, CH$_2$C HOCHO), 3.85 (ddd, 1H, J=6.4, 6.4, and 1.3 Hz, CH$_2$C HOCHOCH$_a$H$_b$), 3.55 (ddd, 1H, J=5.8, 5.8, and 5.8 Hz, C HOHCH$_2$C≡C), 2.94 (ddd, 1H, J=4.2, 4.2, and 1.3 Hz, C HOCH$_a$H$_b$), 2.72 (dd, 1H, J=9.5 and 4.3 Hz, CHOC H$_a$H$_b$), 2.51 (dd, 2H, J=5.2 and 2.8 Hz, CHOCH$_a$H$_b$), 2.62 (d, 1H, J=5.2 Hz, OH), 2.44 (dd, 1H, J=13.4 and 2.8 Hz, CHOHCH$_a$H$_b$C≡C), 2.42 (dd, 1H, J=13.4 and 2.0 Hz, CHOHCH$_a$H$_b$C≡C), 1.89–2.12 (m, 4H, from among C H$_2$CH$_2$), 1.64–1.89 (m, 4H, from among CH$_2$CH$_2$), and 0.10 [s, 9H, Si(CH$_3$)$_3$].

$^{13}$C NMR (125 MHz, CDCl$_3$): δ103.1, 86.5, 82.2, 81.8, 81.3, 78.6, 71.9, 54.1, 44.0, 28.7, 28.6, 28.2+, 2.82−, 25.3, and −0.05

IR (neat, thin layer): 3448, 3071, 3050, 2961, 2900, 2174, 1463, 1421, 1324, 1249, 1105, 1059, 904, and 844 cm$^{-1}$.

Anal. Calcd for C$_{17}$H$_{28}$O$_4$Si: C, 62.93%; H, 8.70%. Found: C, 62.74%; H, 8.81%.

tlc: R$_f$=0.53 in 1:3 hexane:ethyl acetate

[α]$_D^{RT}$=−16.7°, c=2.44 in CHCl$_3$

8b:

$^1$H NMR (500 MHz, CDCl$_3$): δ3.99 (ddd, 2H, J=5.8, 5.8, and 7.9 Hz, CHOCHOH), 3.88 (dd, 2H, J=5.5 and 5.5 Hz, CH$_2$CHOCHOCH$_2$), 3.58 (ddd, 2H, J=5.8, 5.8, and 5.8 Hz, CHOHCH$_2$C≡C), 2.99 (brs, 2H, OH), 2.47 (dd, 2H, J=17.1 and 6.1 Hz, CHOHCH$_a$H$_b$C≡C), 2.44 (dd, 2H, J=17.1 and 6.1 Hz, CHOHCH$_a$H$_b$C≡C), 1.94–2.06 (m, 4H, from among CH$_2$CH$_2$), 1.73–1.83 (m, 2H, from among CH$_2$C H$_2$), 1.61–1.71 (m, 2H, from among CH$_2$CH$_2$), and 0.12 [s, 9H, Si(CH$_3$)$_3$].

$^{13}$C NMR (125 MHz, CDCl$_3$): δ103.2, 86.7, 82.1, 81.6, 72.0, 28.9, 28.3, 25.4, and −0.02.

IR (neat, thin layer): 3426, 2958, 2900, 2175, 1419, 1326, 1249, 1195, 1104, 1058, 949, and 850 cm$^{-1}$.

Anal. Calcd for C$_{22}$H$_{38}$O$_4$Si$_2$: C, 62.51%; H, 9.06%. Found: C, 62.37%; H, 8.97%.

tlc: R$_f$=0.73 in 1:3 hexane:ethyl acetate

[α]$_D^{RT}$=−21.0°, c=3.46 in chloroform

EXAMPLE 12

Preparation of (−)-{2R-[2α[2'R*,5'R*(R*)],5β(R*)]}-α-[3-(trimethylsilyl)-2-propynyl]octahydro-α'-2-decynyl-[2,2'-bifuran]-5,5'-dimethanol (8b)

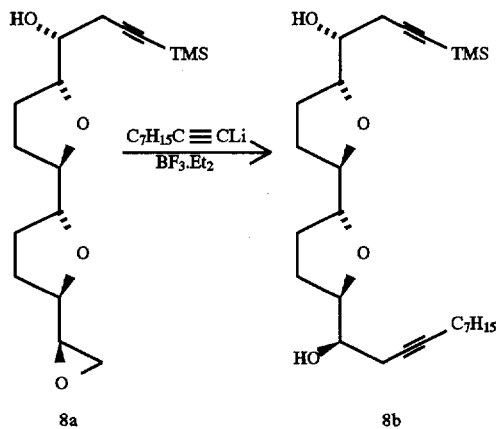

To a solution of nonyne (124 mg, 1.00 mmol) in dry tetrahydrofuran (500 μL) was added n-butyl lithium (400 μL, 2.5M in hexane, 1.00 mmol) at −78° C. The reaction mixture was stirred at −78° C. for 30 min. Boron trifluoride etherate (144 mg, 1.02 mmol) was added slowly. After the reaction mixture was stirred at −78° C. for 15 min, a solution of the epoxide 8a (165 mg, 0.508 mmol) in dry tetrahydrofuran (500 μL) was added slowly at −78° C. After 15 min at −78° C., the reaction mixture was poured into a mixture of diethyl ether (5.0 mL) and a saturated aqueous ammonium chloride solution (5.0 mL). The layers were separated, and the aqueous layer was extracted with diethyl ether (3×5.0 mL). The combined organic extracts were washed with brine, dried over anhydrous magnesium sulfate, filtered, and concentrated. The crude product was purified by MPLC (1:1 hexane:ethyl acetate) to give the alcohol 8b (202 mg, 89%) as a colorless oil; Anal. Calcd for $C_{26}H_{44}O_4Si$: C, 69.60%; H, 9.88%. Found: C, 69.83%; H, 9.91%; tlc: $R_f$=0.70 in 1:1 hexane:ethyl acetate; $[\alpha]_D^{RT}$=−5.6°, c=2.16 in $CHCl_3$

EXAMPLE 13

Preparation of (−)-{2R-[2α[2'R*,5'R*(R*)],5β(R*)]}-α-2-propynyloctahydro-α'-2-decynyl-[2,2'-bifuran]-5,5'-dimethanol (3)

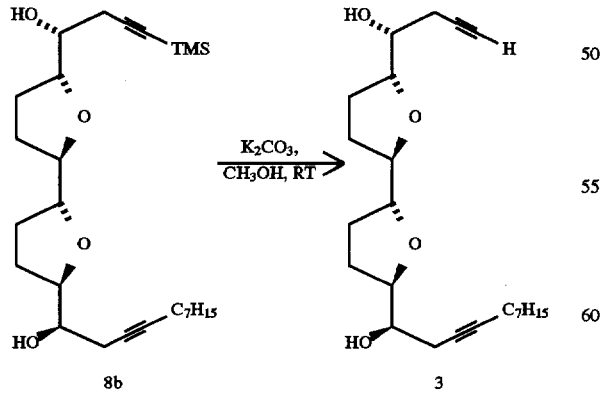

To a solution of the alcohol 8b (128 mg, 285 μmol) in methanol (2.0 mL) was added solid potassium carbonate (12.7 mg, 91.9 μmol) at room temperature. The resulting mixture was stirred for 2.5 h, quenched with a saturated aqueous ammonium chloride solution (10 mL), and extracted with diethyl ether (3×10 mL). The combined organic layers were washed with brine, dried over anhydrous magnesium sulfate, filtered, and concentrated. The crude product was purified by MPLC (1:1 hexane:ethyl acetate) to give the terminal alkyne 3 (106 mg, 99%) as a colorless oil.

$^1$H NMR (500 MHz, $CDCl_3$): δ4.04 (m, 2H, $CH_2C$ HOCHOHCH$_2$C≡CH and CH$_2$CHOC HOHCH$_2$C≡CC$_7$H$_{15}$), 3.90 (m, 2H, CH$_2$CHOCHOCH$_2$), 3.62 [ddd, 1H, J=~5.8, 5.8, and 5.8 Hz, CH(O)C HOHCH$_2$C≡CH], 3.56 [ddd, 1H, J=~5.3, 5.3, and 5.3 Hz, CH(O)CHOHCH$_2$C≡CC$_7$H$_{15}$], 2.85 (br s, 1H, OH), 2.76 (br s, 1H, OH), 2.44 (dd, 2H, J=5.8 and 3.0 Hz, CHOHC H$_2$C≡CH), 2.42 (ddd, 2H, J=6.0, 2.5, and 2.5 Hz, CHOHC H$_2$C≡CC$_7$H$_{15}$), 2.15 (dddd, 2H, J=7.0, 7.0, 2.5, and 2.5 Hz, CH$_2$C≡CCH$_2$C$_6$H$_{13}$), 1.95–2.07 (m, 5H, from among CHOCH$_2$CH$_2$CHO and C≡CH), 1.66–1.82 (m, 4H, from among CHOCH$_2$CH$_2$CHO), 1.47 (dddd, 2H, J=~7.0, 7.0, 7.0, and 7.0 Hz, C≡CCH$_2$CH$_2$C$_5$H$_{11}$), 1.22–1.39 [m, 8H, C≡CCH$_2$CH$_2$(CH$_2$)$_4$CH$_3$], and 0.88 (t, 3H, J=6.7 Hz, CH$_2$CH$_2$CH$_3$).

$^{13}$C NMR (125 MHz, $CDCl_3$): δ82.4, 82.1, 82.0, 81.6, 81.4, 80.7, 75.9, 72.4, 71.9, 70.1, 31.7, 28.9, 28.8$^+$, 28.8$^-$, 28.3$^+$, 28.3$^-$, 24.2, 23.9, 22.6, 18.7, and 14.0.

IR (neat, thin layer): 3429, 3309, 2952, 2929, 2857, 2118, 1458, 1327, 1242, 1195, 1103, 1056, 951, and 876 cm$^{-1}$.

Anal. Calcd for $C_{23}H_{36}O_4$: C, 73.37%; H, 9.64%. Found: C, 73.51%; H, 9.67%.

tlc: $R_f$=0.27 in 1:1 hexane:ethyl acetate
$[\alpha]_D^{RT}$=−20.8°, c=1.30 in chloroform

EXAMPLE 14

Preparation of 1,4-di(5-hexenyloxy)benzene (10)

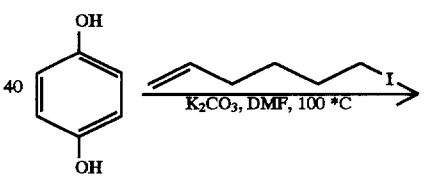

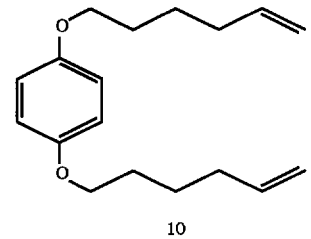

To a 60 mL DMF suspension of potassium carbonate (3.98 g, 28.8 mmol) were added hydroquinone (1.05 g, 9.54 mmol) and 6-iodo-1-hexene (6.01 g, 28.6 mmol) at room temperature. The reaction mixture was warmed to 100° C. and stirred for 10 h. After cooling to room temperature, the mixture was quenched with 10% aqueous sodium hydroxide (60 mL). The mixture was extracted with diethyl ether (3×50 mL). The combined organic solutions were washed with aqueous saturated sodium chloride, dried over anhydrous magnesium sulfate, and concentrated. The crude product was purified by MPLC (80:1, hexane:ethyl acetate) to give the olefin 10 (1.86 g, 71%) as a white solid (mp=29.0°–30.0° C.); Anal. Calcd for $C_{18}H_{26}O_2$: C, 78.79%; H, 9.55%.

Found: C, 78.69%; H, 9.37%; cap gc: $t_R$=10.49 min; column: 25 m×0.25 mm, OV-101;temp prog: 50° C./4 min/20° C. min$^{-1}$/250° C./0 min; tlc: $R_f$=0.48 in 9:1 hexane:ethyl acetate.

EXAMPLE 15

Preparation of (+)-{R-[R*(R*)]}-6-{4-[(5,6-dihydroxyhexyl)oxy]phenoxy}-1,2-hexanediol (11)

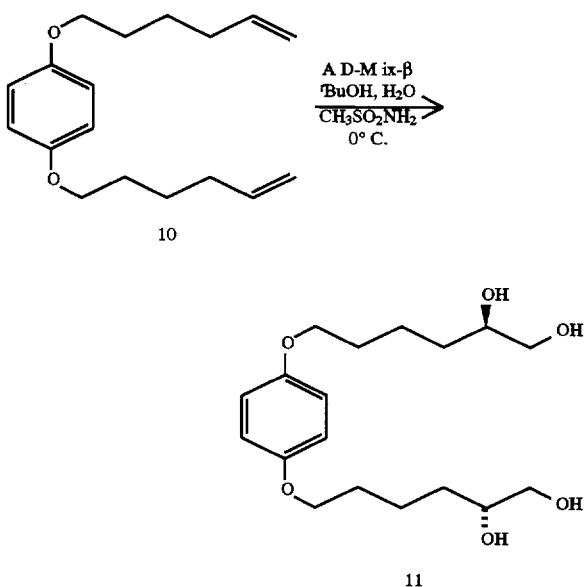

A 150 mL round-bottomed flask, equipped with a magnetic stirrer, was charged with tert-BuOH (30.0 ml), water (30.0 mL), and AD mix-β (8.15 g). Stirring at room temperature produced two clear phases. The mixture was cooled to 0° C. and the olefin 10 (819 mg, 2.98 mmol) was added at once. The heterogeneous slurry was stirred vigorously at 0° C. for 7 h (reaction progress was monitored by TLC). While the mixture was stirred at 0° C., Na$_2$SO$_3$ was added. The mixture was allowed to warm to room temperature and stirred for 1 h. Ethyl acetate (50 mL) was added to the reaction mixture. The aqueous layer was further extracted with ethyl acetate (3×50 mL) and an ethyl acetate/ethanol mixture (4:1) (3×50 mL). The combined organic layers were dried over anhydrous magnesium sulfate and concentrated to give a white solid. The crude product was recrystallized twice in ethyl acetate to yield the alcohol 11 (633 mg, 62%) as a white solid (mp=105.0°–105.5° C.); IR (KBr pellet): 3351, 2949, 2938, 2858, 1515, 1473, 1462, 1397, 1294, 1236, 1119, 1041, 1025, 1003, and 827 cm$^{-1}$; Anal. Calcd for C$_{18}$H$_{30}$O$_6$: C, 63.14%; H, 8.83%. Found: C, 63.15%; H, 8.78%; tlc: $R_f$=0.45 in 4:1 ethyl acetate:ethanol; [α]$_D^{RT}$=+ 11.9°, c=5.44 in methanol.

EXAMPLE 16

Preparation of (+)-{R-[R*(R*)]}-{4-[4-(4-oxiranyl)butoxy]phenoxy}butyloxirane (12)

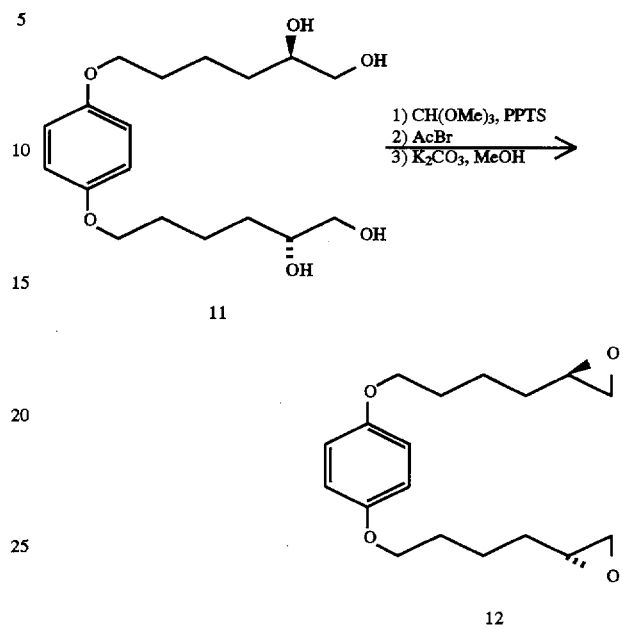

Trimethyl orthoacetate (1.36 g, 12.8 mmol) was added to a solution of the alcohol 11 (1.36 g, 3.97 mmol) in methylene chloride (30 mL) followed by pyridinium p-toluenesulfonate (30.0 mg, 0.119 mmol). The mixture was stirred for 30 min at room temperature, the volatiles were evaporated, and the residual methanol was removed under high vacuum for 10 min. The residue was redissolved in methylene chloride (20 mL), the solution was cooled to 0° C., and acetyl bromide (800 μL, 10.8 mmol) was introduced dropwise via syringe. After 1.5 h at 0° C., TLC showed the reaction was complete and the solvent was evaporated. The residue was dissolved in methanol (40 mL), and potassium carbonate was added to the vigorously stirred solution. After 1 h at 35° C., the mixture was poured into a saturated aqueous ammonium chloride solution and extracted with methylene chloride (4×50 mL). The combined organic layers were dried over anhydrous magnesium sulfate, filtered, and concentrated. The crude product was purified by MPLC (2:1 hexane:ethyl acetate) to give the epoxide 12 (1.12 g, 92%) as a white solid (mp=39.0°–39.5° C.); Anal. Calcd for C$_{18}$H$_{26}$O$_4$: C, 70.56%; H, 8.55%. Found: C, 70.49%; H, 8.66%; cap gc: $t_R$=12.75 min; column: 25 m×0.25 mm, OV-101; temp prog: 50° C./4 min/20° C. min$^{-1}$/250° C./0 min; tlc: $R_f$=0.56 in 1:1 hexane:ethyl acetate; [α]$_D^{RT}$=+ 12.4°, c=5.45 in ethyl acetate.

EXAMPLE 17

Preparation of (±)-4-trimethylsilyl-3-butyn-2-ol (ii)

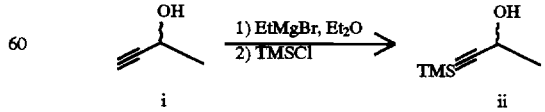

To a solution of 3-butyn-2-ol (i) (2.00 g, 28.5 mmol) in ether (40 mL) was added ethyl magnesium bromide (21.0 mL, 3.0M in tetrahydrofuran, 63.0 mmol) dropwise at 0° C. The resulting solution was refluxed for 1.5 h and cooled to 0° C. Trimethylsilyl chloride (6.85 g, 63.1 mmol) was added. The mixture was then warmed up to room temperature and stirred overnight. Hydrochloric acid (20.0 mL, 10% aqueous solution) was added at 0° C. After 20 min the layers were separated and the aqueous layer was extracted with ether (2×50 mL). The combined organic layers were washed with a saturated aqueous sodium carbonate solution and water, dried over anhydrous magnesium sulfate, filtered, and concentrated. The residue was distilled to give the alcohol ii (3.81 g, 94%, 81°–85° C./20 mmHg) as a colorless liquid; $^1$H NMR (300 MHz, CDCl$_3$): δ4.42 [q, 1H, J=6.6 Hz, CH(OH)CH$_3$], 3.12 [brs, 1H, CH(OH)CH$_3$], 1.16 [d, 3H, J=6.6 Hz, CH(OH)CH$_3$], and 0.08 [s, 9H, Si(CH$_3$)$_3$].

EXAMPLE 18

Preparation of (−)-(S)-4-trimethylsily-3-butyn-2-ol (iii)

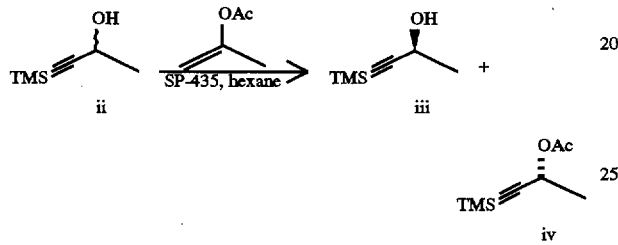

To a solution of the alcohol ii (10.2 g, 71.4 mmol) in hexane (150 mL) was added isopropenyl acetate (34.9 g, 0.342 mol) and SP-435 (1.0 g, Novo Nordisk). The mixture was stirred with a mechanical stirrer for 5 days at 65° C. The enzyme was filtered and washed with pentane (2×50 mL). The filtrates were concentrated and the residue was purified by MPLC (9:1, pentane:ether) to give the alcohol iii (4.13 g, 41%) as a colorless liquid. The spectral data were the same as for alcohol ii; [α]$_D^{RT}$=−25.6°, C=0.59 in chloroform.

EXAMPLE 19

Preparation of (−)-(S)-(1,1-dimethylethyl)dimethyl[(1-methyl-2-propynyl)oxy]silane (13)

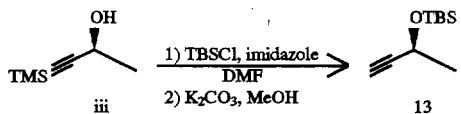

To a solution of the alcohol iii (3.47 g, 24.4 mmol) in N,N-dimethyl formamide (30 mL) was added tert-butyldimethylsilylchloride (4.74 g, 31.4 mmol) and imidazole (3.98 g, 58.5 mmol). The mixture was stirred overnight at room temperature, quenched with water (20 mL), and extracted with diethyl ether (4×50 mL). The combined organic layers were dried over anhydrous magnesium sulfate, filtered, and concentrated. The residue was redissolved in methanol (20 mL) and potassium carbonate (1.00 g, 7.24 mmol) was added. The mixture was stirred at room temperature for 2 h, and transferred to a pad of silica gel (~50 g) and eluted with pentane. The elutes were concentrated to give the alkyne 13 (3.90, 87%) as a colorless liquid; cap gc: t$_R$=2.75 min; column: 25 m×0.25 mm, OV-101; temp prog: 50° C./4 min/20° C. min$^{-1}$/250° C./0 min; tlc: R$_f$=0.21 in hexane; [α]$_D^{RT}$=−46.3°, c=1.4 in chloroform.

EXAMPLE 20

Preparation of (−)-{2S-[2R*,6S*,10(5S*,9R*)]}-2{[(1,1-dimethylethyl)dimethylsilyl]oxy}-10-{4-[[5-hydroxy-9-[[(1,1-dimethylethyl)dimethylsilyl]oxy]-7-decynyl]oxy]phenoxy}-3-decyn-6-ol (12a)

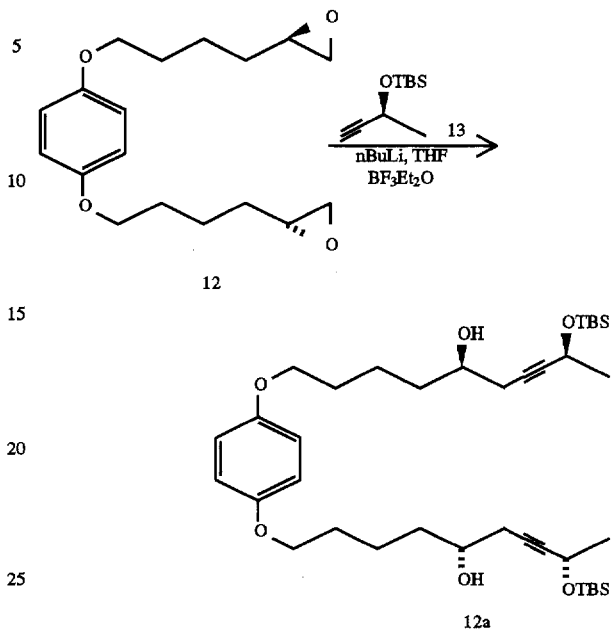

To a solution of the alkyne 13 (403 mg, 2.18 mmol) in tetrahydrofuran (4.0 mL) was added n-butyl lithium (0.90 mL, 2.5M in toluene, 2.25 mmol) at −78° C. under nitrogen. The mixture was stirred for 25 min, and trifluoroboron etherate (270 μL, 2.20 mmol) was added dropwise. After 15 min a solution of the epoxide 12 (228 mg, 742 μmol) in dry tetrahydrofuran (3.0 mL). The mixture was kept at −78° C. for 30 min and poured into a mixture of water (15 mL) and ether (20 mL) was added. The layers were separated and the aqueous layer was extracted with ether (3×20 mL). The combined organic layers were dried over anhydrous magnesium sulfate and concentrated. The crude product was purified by MPLC (1:1, hexane:ethyl acetate) to give the alcohol 12a (446 mg, 89%) as a colorless oil.

$^1$H NMR (500 MHz, CDCl$_3$): δ6.80 (s, 4H, ArH), 4.49 [ddq, 2H, J=1.9, 1.6, and 6.4 Hz, CH(OTBS)CH$_3$], 3.88 (t, 4H, J=6.4 Hz, OCH$_2$CH$_2$), 3.72 [m, 2H, CH$_2$CH(OH)CH$_2$], 2.41 [ddd, 2H, J=16.9, 5.2 and 1.8, CH(OH)CH$_a$H$_b$C], 2.32 [ddd, 2H, CH(OH)CH$_a$H$_b$C], 2.27 [bs, 2H, CH$_2$CH(OH)CH$_2$], 1.70–1.80 (m, 4H, OCH$_2$CH$_2$CH$_2$), 1.44–1.64 [m, 8H, CH$_2$CH$_2$CH$_2$CH(OH)], 1.37 [d, 6H, J=6.7 Hz, CH(OTBS)CH$_3$], 0.88 [s, 18H, SiC(CH$_3$)$_3$], 0.10 [s, 6H, Si(CH$_3$)$_a$(CH$_3$)$_b$], and 0.09 [s, 6H, Si(CH$_3$)$_a$(CH$_3$)$_b$].

$^{13}$C NMR (125 MHz, CDCl$_3$): δ153.1, 115.3, 85.3, 79.8, 69.8, 68.3, 59.1, 35.8, 29.3, 27.7, 25.8, 25.6, 22.2, 18.2, −4.6, and −4.9.

IR (neat, thin layer): 3424, 2950, 2930, 2858, 1508, 1472, 1251, 1230, 1160, 1101, 1085, 1028, 954, and 834 cm$^{-1}$.

Anal. Calcd for C$_{38}$H$_{66}$O$_6$Si$_2$: C, 67.61%; H, 9.85%. Found: C, 67.77%; H, 9.88%.

tlc: R$_f$=0.54 in 1:1 hexane:ethyl acetate.

[α]$_D^{RT}$=−21.8°, c=4.66 in ethyl acetate.

EXAMPLE 21

Preparation of (−)-{2S-[2R*,6S*,10(5S*,9R*)]}-2{[(1,1-dimethylethyl)dimethylsilyl]oxy}-6-{[(1,1-dimethylethyl)diphenylsilyl]oxy}-10-{4-[[5-[[(1,1-dimethylethyl)

diphenylsilyl]oxy]-9-[[(1,1-dimethylethyl)dimethylsilyl]oxy]-7-decynyl]oxy]phenoxy}-3-decyne (12b)

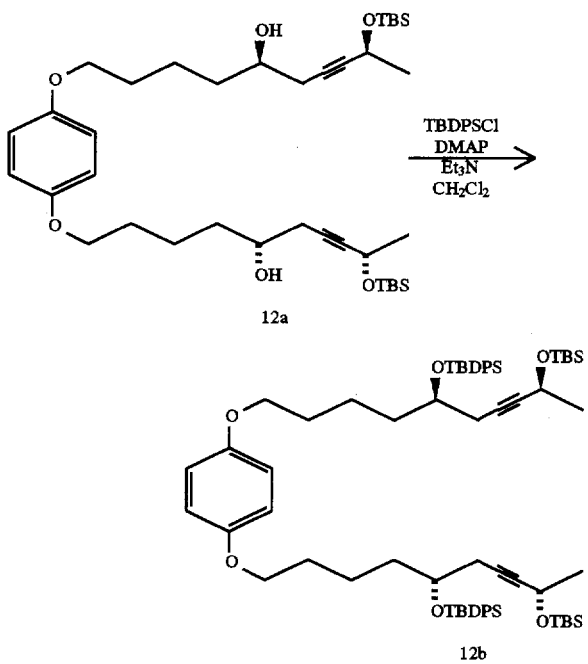

12a

12b

A mixture of the alcohol 12a (416 mg, 616 μmol), tert-butyldiphenylsilylchloride (0.846 g, 3.08 mmol), 4-(N,N-dimethylamino)pyridine (96 mg, 786 μmol), and triethylamine (1.5 mL) in methylene chloride (5.0 mL) were stirred at 40° C. in a sealed culture tube for 2 days. The mixture was quenched with brine and extracted with ether (3×20 mL). The combined organic layers were dried over anhydrous magnesium sulfate, filtered, and concentrated. The crude product was purified by MPLC (19:1 hexane:ethyl acetate) to give the alkyne 12b (590 mg, 83%) as a colorless oil; IR (neat, thin layer): 3071, 3049, 2931, 2893, 2858, 1961, 1892, 1826, 1589, 1507, 1471, 1428, 1364, 1251, 1229, 1161, 1105, 1026, 955, and 833 cm$^{-1}$; Anal. Calcd for $C_{70}H_{102}O_6Si_4$: C, 72.99%; H, 8.93%. Found: C, 72.99%; H, 8.89%; tlc: $R_f$=0.49 in 9:1 hexane:ethyl acetate; $[\alpha]_D^{RT}$=−17.0°, c=4.97 in ethyl acetate.

EXAMPLE 22

Preparation of (−)-{2S-[2R*,6S*,10(5S*,9R*)]}-6{[(1,1-dimethylethyl)diphenylsilyl]oxy}-10-{4-[[5-[[(1,1-dimethylethyl)diphenylsilyl]oxy]-9-hydroxy-7-decynyl]oxy]phenoxy}-3-decyn-2-ol (14)

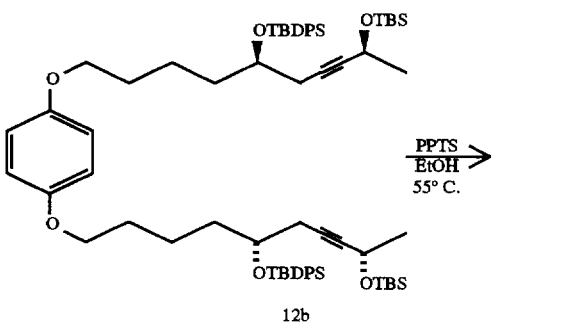

12b

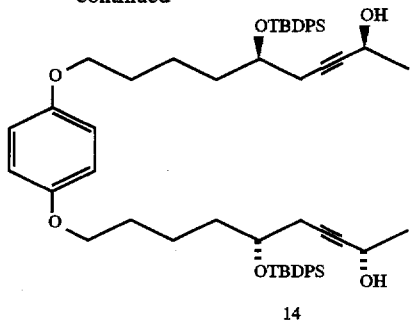

14

To a solution of the alkyne 12b (526 mg, 457 μmol) in absolute ethanol (6.0 mL) was added pyridinium p-toluenesulfonate (273 mg, 1.09 mmol) in one portion. The reaction mixture was stirred at 55° C. overnight (~14 h). The solvent was removed in vacuo and the residue was dissolved in ethyl acetate (50 mL). The organic solution was washed with water and brine, dried over anhydrous magnesium sulfate, filtered, and concentrated. The crude product was purified by MPLC (3:1 hexane:ethyl acetate) to give the alcohol 14 (387 mg, 92%); IR (neat, thin layer): 3405, 3070, 3048, 2935, 2858, 1963, 1893, 1827, 1589, 1507, 1471, 1428, 1365, 1228, 1155, 1002, and 823 cm$^{-1}$; Anal. Calcd for $C_{58}H_{74}O_6Si_2$: C, 75.44%; H, 8.08%. Found: C, 75.16%; H, 7.89%; tlc: $R_f$=0.14 in 3:1 hexane:ethyl acetate; $[\alpha]_D^{RT}$= −7.9°, c=5.47 in ethyl acetate.

EXAMPLE 23

Preparation of (−)-{2S-[2R*,6S*,10(5S*,9R*,7Z),3Z]}-4-iodo-6-{[(1,1-dimethylethyl)diphenylsilyl]oxy}-10-{4-[[5-[[(1,1-dimethylethyl)diphenylsilyl]oxy]-7-iodo-9-hydroxy-7-decenyl]oxy]phenoxy}-3-decen-2-ol (14a)

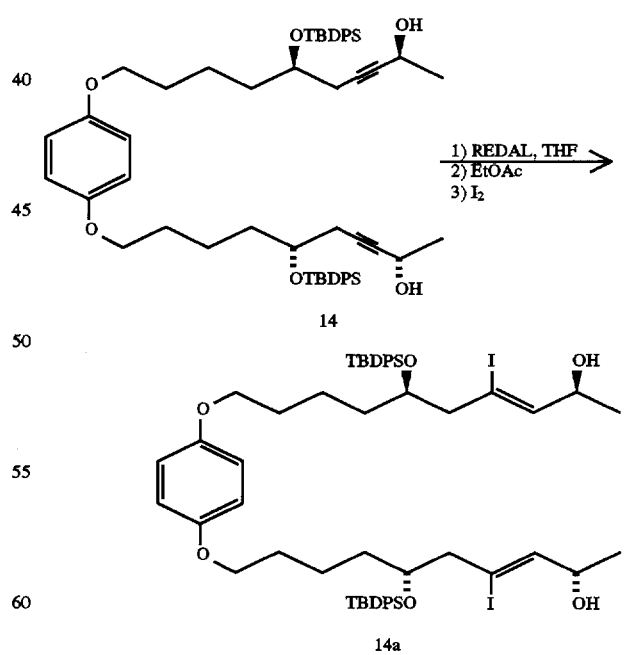

14

14a

To a solution of the alkyne 14 (397 mg, 0.430 mmol) in dry tetrahydrofuran (16 mL), sodium bis(2-methoxyethoxy) aluminum hydride (1.10 mL, 60% in toluene, 3.66 mmol) was added at 0° C. The reaction mixture was stirred for 5 h and ethyl acetate (1.0 mL) was added. The solution was stirred at 0° C. for 20 min, and cooled to −78° C. A solution of iodine (1.01 g, 3.98 mmol) in tetrahydrofuran (10 mL) was added dropwise. The reaction mixture was stirred for another 30 min at −78° C., allowed to warm to room temperature, and quenched with a saturated sodium thiosulfate solution. The organic layer was separated and the aqueous layer was extracted with ether (3×20 mL). The combined organic solutions were washed with a saturated sodium bicarbonate solution and brine, dried over anhydrous magnesium sulfate, filtered, and concentrated. The crude product was purified by MPLC (3:1 hexane:ethyl acetate) to give 14a (448 mg, 88%) as an oil; $^{13}$C NMR (125 MHz, CDCl$_3$): δ153.0, 140.6, 135.9$^+$, 135.9$^-$, 134.0, 133.9, 129.6, 127.6, 127.5, 115.3, 103.9, 72.6, 71.7, 68.2, 51.7, 35.2, 29.2, 27.0, 21.7, 20.8, and 19.4; IR (neat, thin layer): 3400, 3069, 3047, 2932, 2857, 2246, 1960, 1891, 1826, 1589, 1507, 1471, 1427, 1364, 1228, 1109, 909, and 823 cm$^{-1}$; Anal. Calcd for C$_{58}$H$_{76}$I$_2$O$_6$Si$_2$: C, 59.08%; H, 6.50%. Found: C, 59.09%; H, 6.50%; tlc: R$_f$=0.70 in 1:1, hexane:ethyl acetate; [α]$_D^{RT}$=−24.0°, c=6.08 in ethyl acetate.

EXAMPLE 24

Preparation of (−)-{S-[R*,S*,[S*(R*)]}-3-[2-(1,1-dimethylethyl)diphenyl]silyloxy-6-{4-[[5-[[(1,1-dimethylethyl)diphenylsilyl]oxy]-6-[5-methyl-2-oxo-2,5-dihydrofuranyl]hexyl]oxy]phenoxy}-2(5H)-furanone (14b)

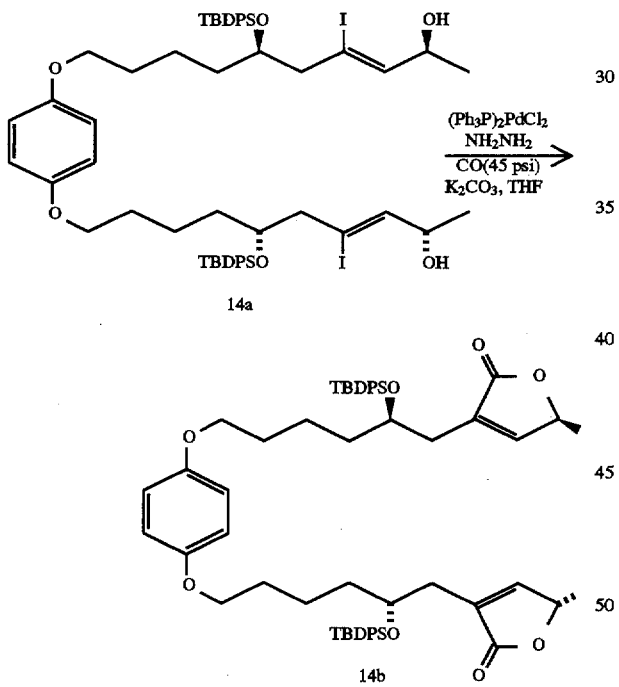

To a mixture of bis(triphenylphosphine)palladium (II) chloride (15.2 mg, 21.7 μmol) and anhydrous potassium carbonate (94.2 mg, 682 μmol) in a carbonylation bomb was added a solution of 14a (402 mg, 341 μmol) in dry tetrahydrofuran (5.0 mL) followed by two drops of hydrazine. The mixture was stirred under a carbon monoxide atmosphere (45 psi) for 2 days at 40° C. Diethyl ether (20 mL) was added and the mixture was filtered. After the solvent was removed, the residue was purified by MPLC (2:1 hexane:ethyl acetate) to give 14b (307 mg, 92%) as a colorless oil.

$^1$H NMR (500 MHz, CDCl$_3$): δ7.66 (m, 8H, ArH), 7.39 (m, 12H, ArH), 6.83 (br s, 2H, CH=C—C=O), 6.65 (s, 4H, Ar'H), 4.83 [br q, 2H, J=7.0 Hz, C=CHCH(O)CH$_3$], 4.03 [dddd, 2H, J=~5.5, 5.5, 5.5, and 5.5 Hz, CH$_2$CH(OTBDPS)CH$_2$], 3.78 (t, 4H, J=6.4 Hz, Ar'OCH$_2$CH$_2$), 2.48 (dd, 2H, J=15.2 and 5.8 Hz, CH$_a$H$_b$C(CO)=CH), 2.44 (dd, 2H, J=15.2 and 5.5 Hz, CH$_a$H$_b$C(CO)=CH), 1.51–1.58 (m, 4H, from among Ar'OCH$_2$CH$_2$CH$_2$), 1.36–1.50 [m, 8H, CH$_2$CH$_2$CH(OTBDPS), 1.30 [d, 6H, J=6.7 Hz, C=CHCH(O)CH$_3$], and 1.04 [s, 18H, SiC(CH$_3$)$_3$].

$^{13}$C NMR (125 MHz, CDCl$_3$): δ173.9, 153.0, 151.3, 135.8$^+$, 135.8$^-$, 134.0, 133.9, 130.5, 129.7$^+$, 129.7$^-$, 127.6, 77.4, 71.5, 68.1, 35.9, 31.8, 29.1, 27.0, 21.3, 19.4, and 18.9.

IR (neat, thin layer): 3070, 3050, 2934, 2859 1964, 1896, 1754, 1589, 1507, 1471, 1429, 1318, 1231, 1108, 1030, and 824 cm$^{-1}$.

Anal. Calcd for C$_{60}$H$_{72}$O$_8$Si$_2$: C, 73.73%; H, 7.42%. Found: C, 73.61%; H, 7.12%.

tlc: R$_f$=0.56 in 1:1, hexane:ethyl acetate.

[α]$_D^{RT}$=−13.2°, c=2.72 in ethyl acetate

EXAMPLE 25

Preparation of (−)-[S-(R*,S*)]-3-{2-[[(1,1-dimethylethyl)diphenylsilyl]oxy]-6-hydroxyhexyl}-5-methyl-2(5H)-furanone (15a)

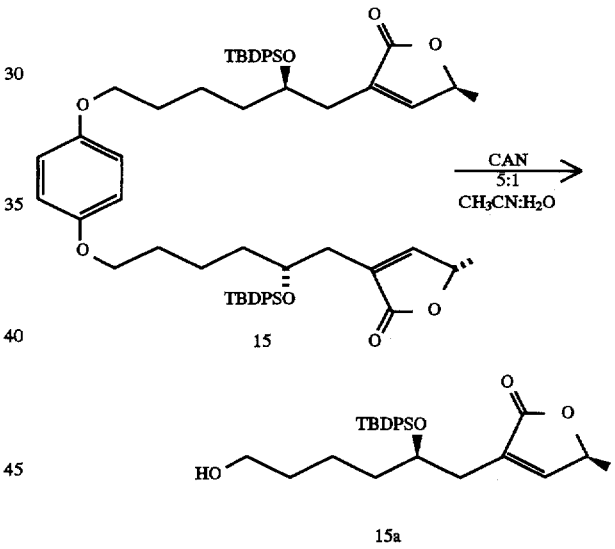

To an ice cooled solution of 15 (35.4 mg, 36.2 μmol) in 5 mL of acetonitrile-water (5:1) was added CAN in one portion. After 10 min the mixture was partitioned between ethyl acetate and brine. The organic layer was separated, washed with a saturated aqueous sodium bicarbonate solution and brine, dried over anhydrous magnesium sulfate, filtered, and concentrated. The crude product was purified by MPLC (1:1, hexane:ethyl acetate) to give 15a (30.2 mg, 92%) as a colorless oil; $^{13}$C NMR (125 MHz, CDCl$_3$): δ174.1, 151.6, 135.8$^+$, 135.8$^-$, 134.0, 133.9, 130.5, 129.7, 127.6, 77.5, 71.6, 62.4, 35.8, 32.3, 31.6, 27.0, 20.8, 19.3, and 18.9; IR (neat, thin layer): 3463, 3071, 3049, 2932, 2859 1963, 1895, 1823, 1747, 1589, 1472, 1428, 1319, 1205, 1108, 1069, 1028, and 822 cm$^{-1}$; Anal. Calcd for C$_{27}$H$_{36}$O$_4$Si: C, 71.64%; H, 8.02%. Found: C, 71.47%; H, 7.88%; tlc: R$_f$=0.39 in 1:1, hexane:ethyl acetate; [α]$_D^{RT}$=−5.85°, c=1.83 in ethyl acetate.

EXAMPLE 26

Preparation of (−)-[S-(R*,S*)]-3-{2-[[(1,1-dimethylethyl)diphenylsilyl]oxy]-6-oxohexyl}-5-methyl-2(5H)-furanone (15a)

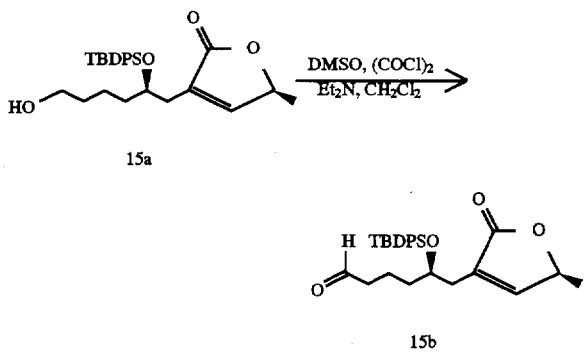

To a solution of DMSO 68.7 mg, 0.879 mmol) in dry methylene chloride (250 μL) was added a solution of oxalyl chloride (200 μL, 2.0M solution in methylene chloride, 0.40 mmol) at −78° C. After stirring at −78° C. for 1 h, a solution of 15a (92.3 mg, 0.209 mmol) in methylene chloride (250 μL) was added dropwise at a fast rate. The resulting solution was stirred at −78° C. for an additional hour. Triethylamine (250 μL) was added and stirred for 30 min. After the mixture was warmed to room temperature, it was quenched with a saturated aqueous ammonium chloride solution. The layers were separated, and the aqueous layer was extracted with methylene chloride (3×5.0 mL). The combined organic layers were washed with brine, dried over anhydrous magnesium sulfate, filtered, and concentrated. The crude product was purified by MPLC (2:1 hexane:ethyl acetate) to give 15b (89.1 mg, 95%) as a colorless oil; IR (neat, thin layer): 3071, 3049, 2953, 2932, 2892, 2857, 2720, 1965, 1898, 1749, 1724, 1589, 1472, 1427, 1318, 1204, 1111, 1067, 1028, and 822 cm$^{-1}$; Anal. Calcd for $C_{27}H_{34}O_4Si$: C, 71.96%; H, 7.60%. Found: C, 71.83%; H, 7.61%; tlc: $R_f$=0.35 in 2:1 hexane:ethyl acetate; $[\alpha]_D^{RT}$=−3.48°, c=2.82 in chloroform.

EXAMPLE 27

Preparation of (−)-{S-[R*,S*(E)]} and (−)-{S-[R*,S*(Z)]}-3-{2-[[(1,1-dimethylethyl)diphenylsilyl]oxy]-7-iodo-6-heptenyl}-5-methyl-2(5H)-furanone (9)

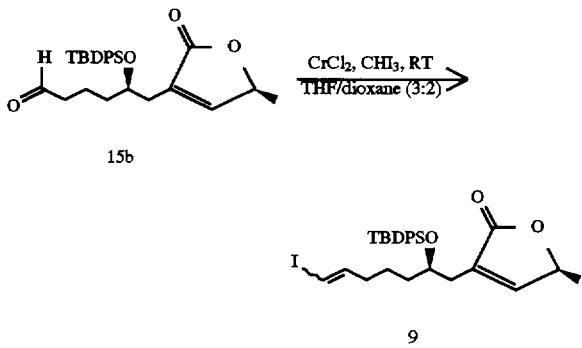

To a suspension of chromous chloride (147 mg, 1.20 mmol) in anhydrous tetrahydrofuran (1.0 mL) was added a solution of 15b (78.5 mg, 0.174 mmol) and iodoform (153 mg, 0.403 mmol) in dry 1,4-dioxane (0.67 mL). After the resulting mixture was stirred at room temperature for 4 h, water (10 mL) was added. The mixture was extracted with ether (3×10 mL). The combined extracts were washed with a saturated aqueous ammonium chloride solution and brine, dried over anhydrous magnesium sulfate, filtered, and concentrated. The crude product was purified by MPLC (3:1 hexane:ethyl acetate) to give 9 (75.2 mg, 75%, 5:1 mixture of E/Z isomers) as a colorless oil; $^{13}C$ NMR (125 MHz, $CDCl_3$): δ173.8, 151.4, 146.0, 140.8 (minor isomer), 135.8$^+$, 135.8$^-$, 133.9, 133.8, 130.4, 129.8, 129.7, 127.6$^+$, 127.6$^-$, 77.4, 74.7, 71.3, 35.6, 35.4, 31.8, 27.0, 23.4, 19.3, and 18.9; IR (neat, thin layer): 3070, 3049, 2931, 2857, 1966, 1895, 1754, 1472, 1427, 1318, 1203, 1111, 1027, and 822 cm$^{-1}$; Anal. Calcd for $C_{28}H_{35}IO_3Si$: C, 58.53%; H, 6.14%. Found: C, 58.61%; H, 6.08%; tlc: $R_f$=0.55 in 2:1 hexane:ethyl acetate; $[\alpha]_D^{RT}$=−16.1°,c=2.66 in ethyl acetate.

EXAMPLE 28

Preparation of (−)-{2R[2α[2'R*,5'R*(R*)],5β[1(S*),2R*,6E,11R*}-3-{2-[((1,1-dimethylethyl)diphenylsilyloxy]-11-hydroxy-11-[octahydro-5'-(1-hydroxyundec-3-ynyl)[2,2'-bifuran]-5-yl]-6-undecen-8-ynyl}-5-methyl-2(5H)-furanone (16) and (?)-{2R-[2α[2'R*,5'R*(R*)],5β[1(S*),2R* ,6Z,11R*}-3-{2-[((1,1-dimethylethyl)diphenylsilyloxy]-11-hydroxy-11 -[octahydro-5'-(1-hydroxyundec-3-ynyl)[2,2'-bifuran]-5-yl]-6-undecen-8-ynyl}-5-methyl-2(5H)-furanone (16)

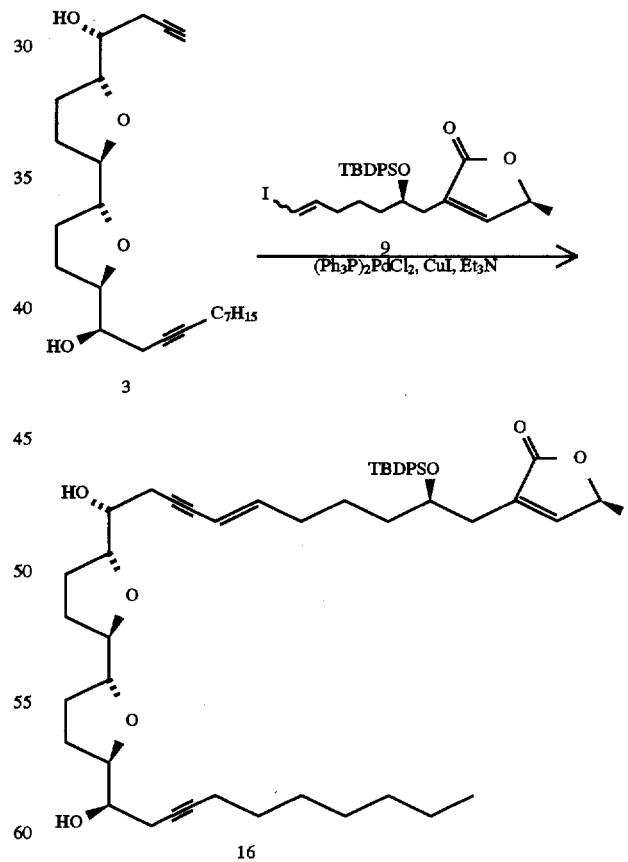

To a stirred solution of 3 (32.1 mg, 85.2 μmol) in triethylamine (1.0 mL) at room temperature was added 9 (84.0 mg, 0.146 mmol), cuprous iodide (5.1 mg, 26.8 μmol), and bis(triphenylphosphine)palladium(II) chloride (6.3 mg, 9.0 μmol). The reaction mixture was stirred overnight at room temperature and diluted with water (5 mL) and ether (5 mL). The organic layer was separated, and the aqueous layer was extracted with ethyl acetate (3×5 mL). The organic layers were combined, washed with brine, dried over anhydrous magnesium sulfate, and concentrated. The residue was purified by MPLC (1:1, hexane:ethyl acetate) to give 16 (57.2 mg, 82%) as an oil.

$^1$H NMR (500 MHz, CDCl$_3$): δ7.65 (m, 4H, ArH), 7.40 (m, 6H, ArH), 6.91 (br s, 1H, CH=C—C=O), 5.86 (ddd, 1H, J=15.8, 7.0, and 7.0 Hz, C≡CCH=CHCH$_2$), 5.33 (ddd, 1H, J=15.8, 1.5, and 1.5 Hz, C≡CCH=CHCH$_2$), 4.89 [br q, 1H, J=7.0 Hz, C≡CHCH(O)CH$_3$], 4.02 [m, 3H, C(4,14,21)H], 3.91 [m, 2H, C(17,18)H], 3.60 [ddd, 1H, J=5.8, 5.8, and 5.8 Hz, C(13)H], 3.56 [ddd, 1H, J=5.3, 5.3, and 5.3 Hz, C(22)H], 2.65 (br s, 1H, OH), 2.61 (br s, 1H, OH), 2.54 [br d, 2H, C(12)H$_2$], 2.42 (dd, 4H, C(3,23)H$_2$), 2.14 [m, 3H, from among C(15,16,19,20)H$_2$], 1.95–2.07 [m, 5H, from among C(15,16,19,20)H$_2$], 1.86 (ddd, 2H, J=7.0, 7.0, and 7.0 Hz, C≡CCH=CHCH$_2$), 1.66–1.82 [m, 6H, C(5,6,26)H$_2$], 1.32 [d, 3H, J=7.0 Hz, C=CHCH(O)CH$_3$], 1.22–1.52 [m, 10H, C(27–31)H$_2$], 1.04 [s, 9H, SiC(CH$_3$)$_3$], 0.88 (t, 3H, J=6.7 Hz, CH$_2$CH$_2$CH$_3$).

$^{13}$C NMR (125 MHz, CDCl$_3$): δ173.9, 151.3, 143.4, 135.8$^+$, 135.8$^-$, 133.9, 130.4, 129.7$^+$, 129.7$^-$, 127.6$^+$, 127.6$^-$, 109.8, 84.5, 82.5, 82.1, 82.0, 81.6, 81.5, 80.9, 77.4, 75.9, 72.4, 72.3, 71.4, 35.6, 32.6, 31.8, 31.7, 28.9, 28.8$^+$, 28.8$^-$, 28.3, 27.0, 24.9, 24.2, 23.9, 22.6, 19.3, 18.9, 18.7, and 14.0.

IR (neat, thin layer): 3463, 3071, 3049, 2929, 2857, 1966, 1895, 1756, 1472, 1428, 1318, 1202, 1110, 1058, 955, and 822 cm$^{-1}$.

HRMS (FAB) calcd for C$_{51}$H$_{71}$SiO$_7$ [M+H]+: 823.4969. Found: 823.4984.

tlc: R$_f$=0.27 in 1:1 hexane:ethyl acetate

[α]$_D^{RT}$=−27.2°, c=0.865 in chloroform

EXAMPLE 29

Preparation of (−)-{2R-[2αc[2'R*,5'R*(R*)],5β[1(S*),2R*,11R*}-3-{2-[(1,1-dimethylethyl)diphenylsilyloxy]-11-hydroxy-11-[octahydro-5'-(1-hydroxyundecyl)[2,2'-bifuran]-5-yl]undecyl}-5-methyl-2(5H)-furanone (16a)

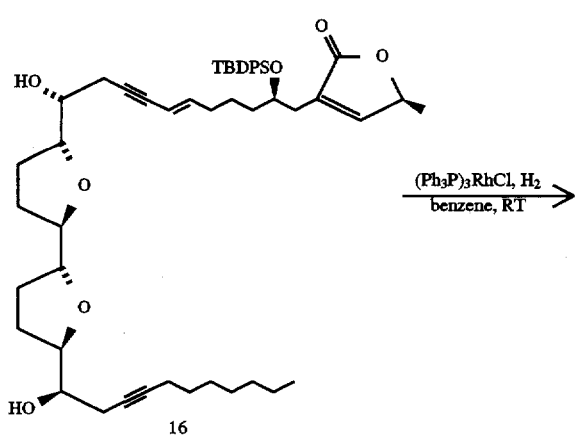

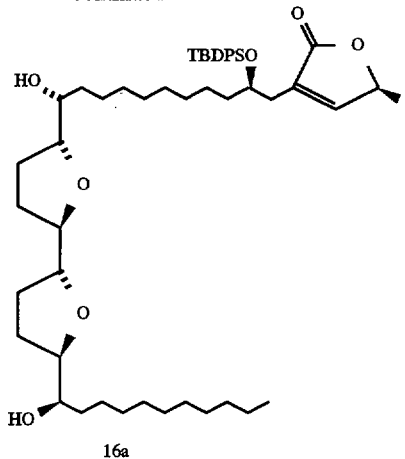

To a stirred solution of 16 (9.5 mg, 12 µmol) in benzene (200 µL) at room temperature was added tris(triphenylphosphine)rhodium(I) chloride (4.6 mg, 5.0 µmol). The system was flushed with Argon gas and the charged with hydrogen gas. After 2 days at room temperature the reaction mixture was diluted with water (2.0 mL) and ether (2.0 mL), the organic layer was separated, and the aqueous layer was extracted with ethyl acetate (3×2.0 mL). The organic layers were combined, washed with brine, dried over anhydrous magnesium sulfate, and concentrated. The residue was purified by MPLC (2:1 hexane:ethyl acetate) to give 29 (6.8 mg, 71%) as an oil; $^{13}$C NMR (125 MHz, CDCl$_3$): δ174.1, 151.1, 135.8$^+$, 135.8$^-$, 133.9, 130.6, 129.7$^+$, 129.7$^-$, 127.6$^+$, 127.6$^-$, 83.1, 82.1, 82.0, 81.6, 81.5, 77.5, 74.1, 74.0, 71.4, 33.4, 31.8, 31.7, 28.9, 28.8$^+$, 28.8$^-$, 28.3, 27.0, 24.9, 24.2, 23.9, 22.6, 19.3, 18.9, 18.7, and 14.0; IR (neat, thin layer): 3466, 3071, 3049, 2927, 2854, 1966, 1895, 1754, 1641, 1463, 1427, 1318, 1202, 1111, 1058, 957, and 822 cm$^{-1}$; HRMS (FAB) calcd for C$_{51}$H$_{81}$SiO$_7$ [M+H]+: 833.5751. Found: 833.5763; tlc: R$_f$=0.46 in 1:1, hexane:ethyl acetate; [α]$_D^{RT}$=−4.7°, c=0.47 in chloroform.

EXAMPLE 30

Preparation of (+)-{2R-[2α[2'R*,5'R*(R*)],5β[1(S*),2R*,11R*}-3-{2,11-dihydroxy-11-[octahydro-5'-(1-hydroxyundecyl)[2,2'-bifuran]-5-yl]undecyl}-5-methyl-2(5H)-furanone (1a, Parviflorin)

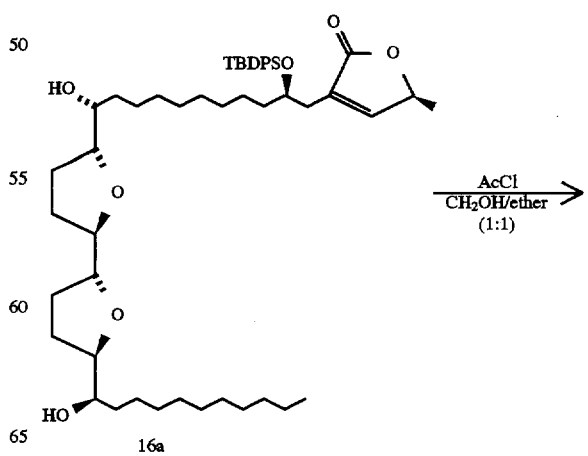

-continued

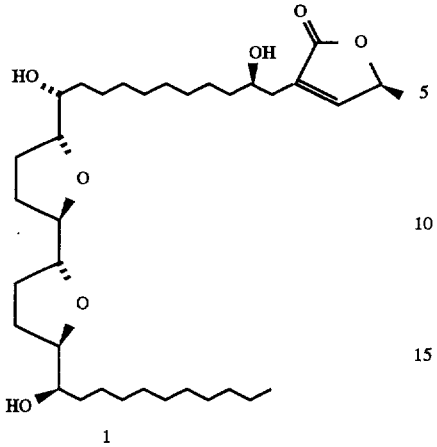

To a solution of acetyl chloride (20 μL) in 400 μL of methanol, a solution of 16a (6.8 mg, 8.2 μmol) in 400 μL of diethyl ether was added at room temperature. The solution was stirred at room temperature until TLC showed that no more starting material was left (about 24 h). Solid sodium bicarbonate was slowly added until no more gas evolution was observed. The mixture was concentrated under reduced pressure. Diethyl ether (5 mL) was added, and the resulting solution was washed with brine, dried over anhydrous magnesium sulfate, filtered, and concentrated. Purification by MPLC (1:3 hexane:ethyl actate) give 1a (4.0 mg, 82%) as a white solid.

$^1$H NMR (500 NHz, DCDl$_3$); δ7.18 (br s, 1H, CH=C—C=O), 5.05 [br q, 1H, J=7.0 Hz, C=CHCH(O)CH$_3$], 3.81–3.89 [m, 5H, C(4,14,17,18,21)H], 3.38 [m, 2H, C(13,22)H], 2.52 [dd, 1H, J=15.0 and 3.4 Hz, C(3)H$_a$H$_b$], 2.40 [dd, 1H, J=15.0 and 8.1 Hz, C(3)H$_a$H$_b$], 1.9–2.0 [m, 5H, from among C(15,16,19,20)H$_2$], 1.60–1.72 [m, 3H, from among C(15,16,19,20)H$_2$], 1.43–1.53 [m, 6H, C(5,12,23)H$_2$], 1.42 [d, 3H, J=7.0 Hz, C=CHCH(O)CH$_3$], 1.25–1.41 [m, 28H, C(6–11,24–31)H$_2$], 0.88 (t, 3H, J=7.0 Hz, CH$_2$CH$_2$CH$_3$).

$^{13}$C NMR (125 MHz, CDCl$_3$): δ174.6, 151.7, 131.2, 83.1, 83.0, 81.7, 81.6, 78.0, 74.1, 74.0, 70.0, 33.6, 33.4, 31.8, 31.7, 28.9, 28.8$^+$, 28.8$^-$, 28.3, 27.0, 24.9, 24.2, 23.9, 22.7, 19.2, and 14.1.

IR (neat, thin layer): 3460, 3071, 3049, 2929, 2857, 1966, 1895, 1756, 1472, 1428, 1318, 1202, 1110, 1058, 955, and 822 cm$^{-1}$.

HRMS (FAB) calcd for C$_{35}$H$_{63}$O$_7$ [M+H]+: 595.4474. Found: 595.4481.

tlc: R$_f$=0.36 in 1:3 hexane:ethyl acetate $[\alpha]_D^{RT}$=17.7°, c=0.56 in chloroform All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of the formula:

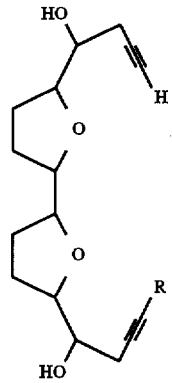

wherein R is H, alkyl or aryl.

2. A compound of claim 1 of the formula:

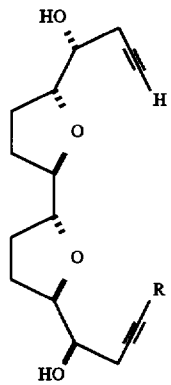

where R is H or alkyl.

3. A compound of claim 2 where R is (C$_4$–C$_{10}$)alkyl.

4. A method for preparing a compound of formula (I):

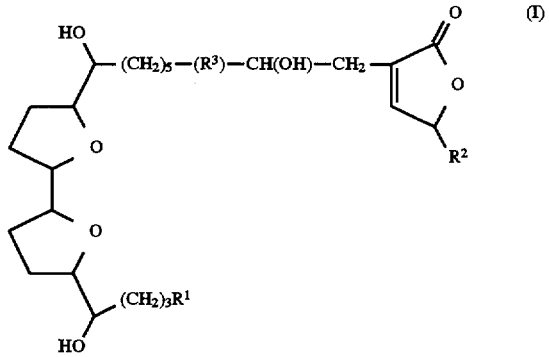

wherein R$^1$, R$^2$ and R$^3$ are alkyl or aryl; comprising:
(a) coupling a vinyl iodide of formula II:

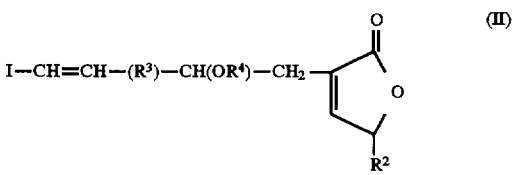

wherein R$^4$ is a removable hydroxy protecting group, with a compound of formula(III):

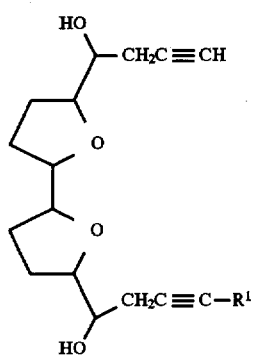

in the presence of an effective amount of a palladium catalyst, CuI and a base, in an organic solvent, to yield an enyne of the formula IV:

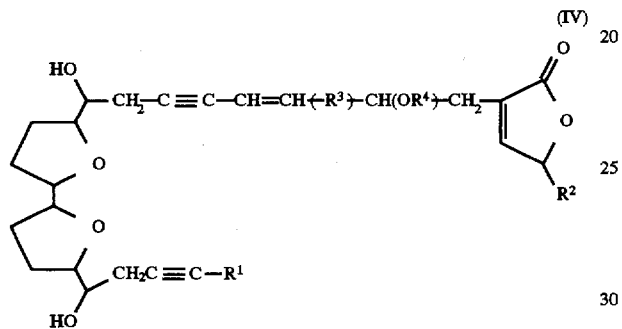

and (b) hydrogenating the enyne of formula IV and removing the hydroxy protecting group to yield a compound of formula I.

5. The method of claim 4 wherein $R^1$, $R^2$ and $R^3$ are alkyl. $R^1$, $R^2$ and $R^3$ are alkyl.

6. The method of claim 4 wherein $R^3$ is —$(CH_2)_n$— and n is 2–10.

7. The method of claim 6 wherein n is 3–7.

8. The method of claim 6 wherein $R^1$ is $C_1$–$C_{18}$.

9. The method of claim 4 wherein $R^2$ is ($C_1$–$C_4$) alkyl.

10. The method of claim 9 wherein the compound of formula I is (+)-asimicin, (+)-bullatacin or (+)-parviflorin.

* * * * *

UNITED STATES PATENT AND TRADEMARK OFFICE
CERTIFICATE OF CORRECTION

PATENT NO.    :    5,677,467

DATED         :    October 14, 1997

INVENTOR(S) :    Thomas R. Hoye

It is certified that error appears in the above-identified patent and that said Letters Patent is hereby corrected as shown below:

At Col. 34, line 7, please delete "$R^1$, $R^2$ and $R^3$ are alkyl.".

Signed and Sealed this

Seventh Day of April, 1998

Attest:

BRUCE LEHMAN

*Attesting Officer*    Commissioner of Patents and Trademarks